US007474184B1

(12) United States Patent
Humphries et al.

(10) Patent No.: US 7,474,184 B1
(45) Date of Patent: Jan. 6, 2009

(54) HYBRID MAGNET DEVICES FOR MOLECULE MANIPULATION AND SMALL SCALE HIGH GRADIENT-FIELD APPLICATIONS

(75) Inventors: David E. Humphries, El Cerrito, CA (US); Seok-Cheol Hong, Seoul (KR); Nicholas R. Cozzarelli, Berkeley, CA (US); Linda A. Cozzarelli, legal representative, Berkeley, CA (US); Martin J. Pollard, El Cerrito, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 11/355,462

(22) Filed: Feb. 15, 2006

Related U.S. Application Data

(60) Provisional application No. 60/653,377, filed on Feb. 15, 2005.

(51) Int. Cl.
*H01F 7/02* (2006.01)
*G01N 33/553* (2006.01)

(52) U.S. Cl. ........................ 335/306; 335/296; 436/526

(58) Field of Classification Search ......... 335/302–306, 335/296; 210/222, 695; 436/526
See application file for complete search history.

(56) References Cited

U.S. PATENT DOCUMENTS

| | | | | |
|---|---|---|---|---|
| 5,897,783 | A * | 4/1999 | Howe et al. | 210/695 |
| 6,954,128 | B2 | 10/2005 | Humphries et al. | |
| 7,148,778 | B2 | 12/2006 | Humphries et al. | |
| 2004/0004523 | A1* | 1/2004 | Humphries et al. | 335/296 |
| 2007/0182517 | A1 | 8/2007 | Humphries et al. | |

OTHER PUBLICATIONS

Strick, T.R., J.F. Allemand et al., "The Elasticity of a Single Supercoiled DNA Molecule", Science, vol. 271 (5257), p. 1835-37 (1996).

Haber, C., Wirtz, D., "Magnetic Tweezers for DNA Manipulation", Review of Scientific Instruments, vol. 71, p. 4561-69 (2000).

Gosse, C., Croquette, V., "Magnetic Tweezers: Micromanipulation and Force Measurement Oat the Molecular Level", Biophysical Journal, vol. 82(6), p. 3314-29 (2002).

Yan, J., D. Skoko et al., "Near-Field-Magnetic-Tweezer Manipulation of Single DNA Molecules." Physical Review E. vol. 70, p. 011905 (2004).

Zlatanova, J., Leuba, S. H., "Magnetic Tweezers: a Sensitive Tool to Study DNA and Chromatin at the Single-Molecule Level." Biochemistry and Cell Biology, vol. 81(3), p. 151-59 (2003).

Hosu, B.G., K. Jakab et al., Magnetic Tweezers for Intracellular Applications, Review of Scientific Instruments, vol. 74, No. 9, p. 4158-63 (Sep. 2003).

* cited by examiner

*Primary Examiner*—Ramon M Barrera
(74) *Attorney, Agent, or Firm*—Lawrence Berkeley National Laboratory; Michelle Chew Wong

(57) ABSTRACT

The present disclosure provides a high performance hybrid magnetic structure made from a combination of permanent magnets and ferromagnetic pole materials which are assembled in a predetermined array. The hybrid magnetic structure provides means for separation and other biotechnology applications involving holding, manipulation, or separation of magnetizable molecular structures and targets. Also disclosed are hybrid magnetic tweezers able to exert approximately 1 nN of force to 4.5 μm magnetic bead. The maximum force was experimentally measured to be ~900 pN which is in good agreement with theoretical estimations and other measurements. In addition, a new analysis scheme that permits fast real-time position measurement in typical geometry of magnetic tweezers has been developed and described in detail.

12 Claims, 35 Drawing Sheets

SECTION A-A

HYBRID MAGNET DEVICES FOR MOLECULE MANIPULATION AND SMALL SCALE HIGH GRADIENT-FIELD APPLICATIONS

CROSS-REFERENCE TO RELATED APPLICATIONS

This application claims priority from U.S. Provisional Patent Application, 60/653,377, filed on Feb. 15, 2005, hereby incorporated by reference in its entirety. This application is also related to U.S. patent application Ser. No. 10/305,658, filed on, Nov. 26, 2002 now issued U.S. Pat. No. 6,954,128 and co-pending continuation-in-part U.S. patent application Ser. No. 11/248,934, filed on Oct. 11, 2005, both of which are incorporated by reference.

STATEMENT OF GOVERNMENTAL SUPPORT

This invention was made during work supported by U.S. Department of Energy under Contract No. DE-AC03-76SF00098, now DE-AC02-05CH11231. The government has certain rights in this invention.

BACKGROUND OF THE INVENTION

1. Field of the Invention

The present invention relates to apparatus and methods for capture, separation, manipulating, measurement, and analysis of micro and nanoparticles and molecular targets.

2. Related Art

Biophysics has been revolutionized in the past decade. In particular, single molecule biophysics allows us to study many biological reactions in quantitative and physical standpoint by directly measuring physical properties of and mechanical interactions among biological molecules (biomolecules) such as DNA and proteins (Svoboda and Block 1994; Ludwig 1999; Mehta, Rief et al. 1999; Bustamante, Macosko et al. 2000). Such a breakthrough was made possible by a number of new methods for manipulating single biomolecules. New manipulation tools are making it possible to follow, in real time and at a single molecule level, the movements, forces, and strains that develop during the course of a reaction because they can exert external forces at appropriate levels to modify the conformation of biomolecules, and highly sensitive detectors can measure the forces and displacements with high spatial and temporal resolutions.

These innovative tools expand the horizon of research areas and convert biological problems that were previously intractable into answerable questions. These biological problems include protein folding (Carrion-Vazquez, Oberhauser et al. 1999), DNA elasticity (Smith, Finzi et al. 1992; Marko 1995), the protein-induced bending of DNA (Erie, Yang et al. 1994), the stress-induced catalysis of enzymes (Wuite, Smith et al. 2000), the behavior of molecular motors (Kishino and Yanagida 1988; Howard, Hudspeth et al. 1989; Ishijima, Doi et al. 1991; Svoboda, Schmidt et al. 1993; Strick, Croquette et al. 2000; Wuite, Smith et al. 2000; Smith, Tans et al. 2001; Stone, Bryant et al. 2003), the protein-protein interaction (Nakajima, Kunioka et al. 1997), and the protein-induced DNA condensation (Case, Chang et al. 2004). Hence, developing new experimental methods is as crucial as clarifying mechanisms of individual biological phenomena in advance of biology.

Among many ingenious methods for single molecule biophysics, laser tweezers and magnetic tweezers are the two most interesting ones. Different from scanning force microscopy (Rief, Gautel et al. 1997; Carrion-Vazquez, Oberhauser et al. 1999) and glass needle method (Ishijima, Doi et al. 1991; Cluzel, Lebrun et al. 1996), the two methods can apply physiologically relevant, low level of force to biomolecules in biological environment. Different from hydrodynamic manipulation (Perkins, Smith et al. 1995), they can control biomolecules in well-defined, fast, and sophisticated manner.

Although magnetic tweezers are superior to laser tweezers in applying torque and sub-pN level of force and are much simpler than laser tweezers, it has remained a rather complementary tool to laser tweezers due to low upper limit of force and geometrical restriction that results in slow position measurement of the vertical dimension Z through diffraction ring analysis (Gosse and Croquette 2002). Another basic design for the magnetic tweezers was reported by Strick, Allemand et al., The elasticity of a single supercoiled DNA molecule, Science; 1996 Mar. 29; 271(5257):1835-7. Since magnetic force pulls magnetic-bead-tagged molecules from the above in most magnetic tweezers apparatus, important information such as DNA extension should be extracted from the Z position measurement (Strick, Allemand et al. 1996).

In order to overcome such obstacles, numerous modifications have been adopted. To increase the force maximum, a bigger bead with higher magnet content was used; a large drag on such beads makes their response slower, which limits the time resolution in the experiment. As an alternative approach, a tiny magnet piece was placed in proximity of a magnetic-bead-tagged molecule to obtain ~200 pN with 2.8 μm magnetic bead {Yan and Marko 2004}. In this method, the extension of interest appears on the view plane similar to laser tweezers and is therefore easier to measure. In spite of these advantages, torque cannot be applied, force calibration via the calibration of pipette stiffness is required each time of experiment, and the system is more sensitive to environmental noise because the work has been demonstrated in open cell geometry.

One way of alleviating the aforementioned geometrical restriction is to change the geometry so that the position measurement on the view plane (X and Y) yields sufficient information to understand the conformation of biomolecules (Leuba, Karymov et al. 2003; Zlatanova and Leuba 2003). For the goal, a horizontal force component can be introduced from buffer flow or asymmetrically positioned magnets. The horizontal force component will tilt magnetic-bead-tagged molecules, which alleviates the need to analyze the vertical dimension and therefore speeds up the analysis. However, this method relies on additional measurements or assumptions.

As a new method, electromagnets have been employed in magnetic tweezers for better control of magnetic field and the position of magnetic particles (Haber 2000; Gosse and Croquette 2002). With electromagnets, even purely horizontal force can be generated by sophisticated feedback operation of 6 electromagnets and canceling gravitational force (Gosse and Croquette 2002). Although it permits fast and complex operations for positioning a particle precisely in 3D, the force is weak and electromagnets will require extensive cooling for higher force. All these modifications have overcome some of the obstacles but produced new ones.

A related hybrid magnet structure was previously developed in Lawrence Berkeley National Laboratory and Joint Genome Institute (JGI: Department of Energy) for use in biotechnology applications and is described in now issued U.S. Pat. No. 6,954,128 and continuation-in-part U.S. patent application Ser. No. 11/248,934, filed on Oct. 11, 2005, and is hereby incorporated in its entirety.

Herein are described hybrid magnetic tweezers and its use as a more powerful and versatile tool. A new analysis scheme utilizing Hilbert transformation makes it fast to determine the Z position in spite of the same geometrical restriction.

BRIEF SUMMARY OF THE INVENTION

The present invention provides high performance hybrid magnetic tweezers, made from a combination of permanent magnets and soft ferromagnetic materials, useful for manipulation, measurement, study or analysis of molecular targets and micro- and nanoparticles.

The hybrid magnetic tweezers are generally comprised of mirror image single or multi-pole hybrid magnetic structures, which comprise a non-magnetic base, a ferromagnetic pole having a wedge-shaped tip with a notch or concavity at the tip, and at least two blocks of permanent magnet material, assembled onto the base on opposite sides of and adjacent to the ferromagnetic pole in a periodic array, wherein the magnetization orientations of the blocks oriented in opposing directions and orthogonal to the height of the ferromagnetic pole. The blocks of permanent magnet material should extend beyond the edge of the ferromagnetic pole when assembled onto the base.

The hybrid magnetic structure preferably further comprises a retainer adjacent the outermost block of magnetic material. The non-magnetic base is preferably a non-magnetic material such as aluminum. The ferromagnetic pole should be made soft ferromagnetic materials such as steel, low-carbon steel or vanadium pemendur. The pole tip of the ferromagnetic pole can be shaped to create unique field gradients. The pole tip can be shaped so as to produce high fields and gradients in a localized region for the purpose of single molecule manipulation. The blocks of permanent magnet material are preferably comprised of a rare earth element, such as neodymium iron boron or samarium cobalt. Special bonding fixtures may be needed to hold the magnets and mechanically restrain the components during assembly of the hybrid magnetic structure because of the high field strengths.

In a preferred embodiment, a gap exists between the facing mirror image hybrid magnetic structures. In another embodiment, the retainer and non-magnetic base further comprise a means for adjusting the gap between the hybrid magnetic structures.

In one embodiment, the hybrid magnetic tweezers are housed in a clevis having guidance and orientation control.

In another preferred embodiment, the hybrid magnetic tweezers are used in a tweezers apparatus further comprising a light source, collimating optics with a set of lenses, a rotation/translation assembly with manual or computer controls, a flow cell containing the target, the target comprising a molecule or particle having a magnetic bead attached, an objective lens and a CCD camera. Target molecules and particles inside the flow cell can be mechanically manipulated by applying force and torque via the magnetic bead attached to them. In such an embodiment, the hybrid magnetic tweezers should be capable of rotation to induce torque force on the magnetic beads attached to the targets. The force by hybrid magnetic tweezers may vary depending on Z position of the ferromagnetic poles and pole tip.

The hybrid magnetic structure should have a magnetic field strength of at least 6000 Gauss, preferably 8000 Gauss, and even more preferably a magnetic field strength of 1 Tesla. This translates to the hybrid magnetic tweezers capable of exerting a force on a target of at least 10 picoNewtons to 1 nanoNewton.

BRIEF DESCRIPTION OF THE DRAWINGS

FIG. 10A Inset: (left) a diffraction image from a magnetic bead; (right) one from a pipette. (B) Q'[x] is a radial intensity profile after filtering or real part of Hilbert transform of the profile Q[x] (FIG. 2A). The intensity values were shifted due to omission of the zero-frequency term in the transformations. Inset: the parametrized plot of Q'[x] and I[x] using the data labeled in blue in (A). (c) Phase Φ[x] from Hilbert transform vs. x. Each Φ[x] was averaged over the range indicated with the box. (D) Average phase ϕ vs. relative Z distance. The line is a cubic fit.

DETAILED DESCRIPTION OF THE PREFERRED EMBODIMENT

Figure 1A:
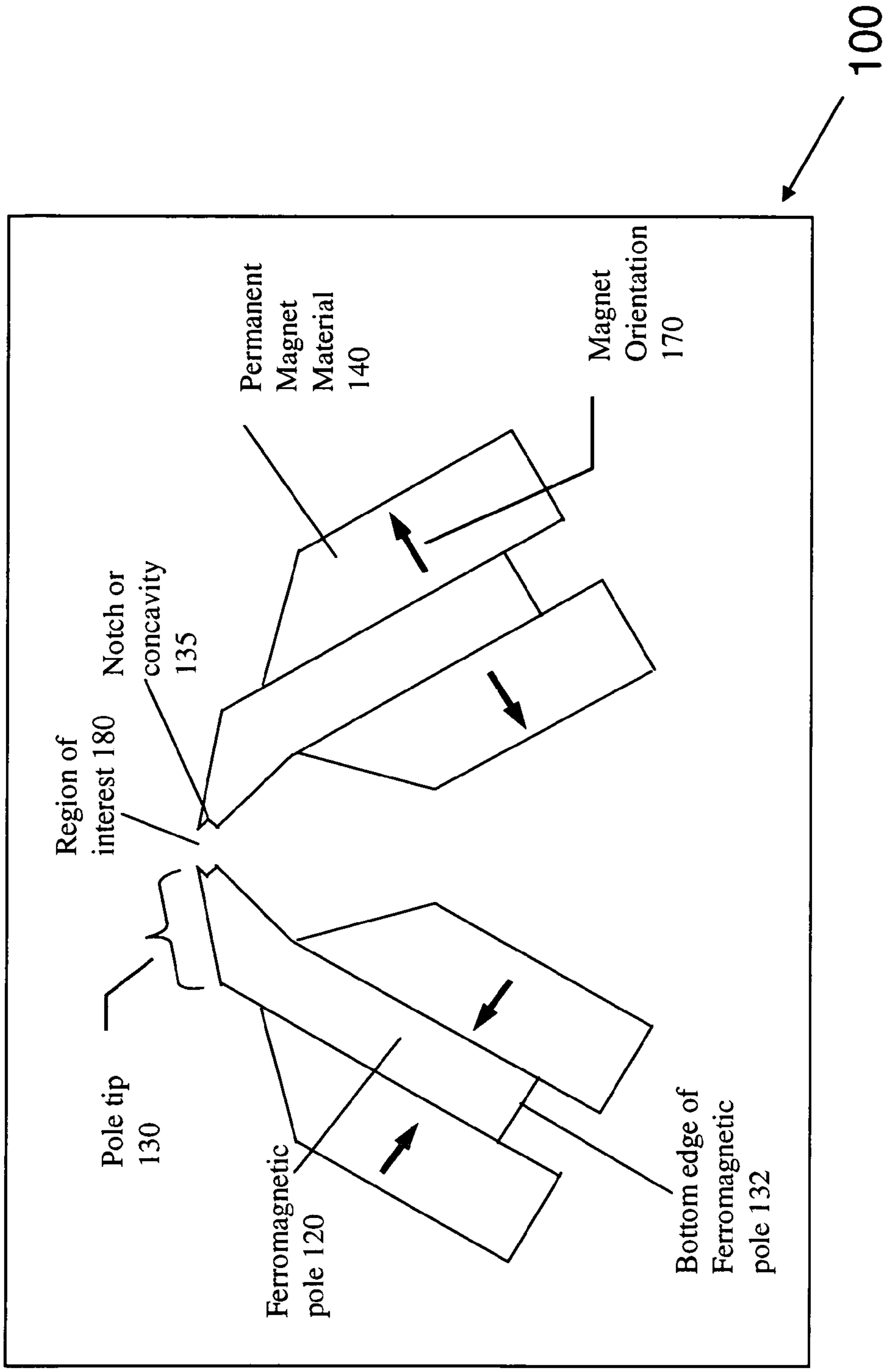
FIG. 1A is a cross-sectional view of two hybrid magnetic structures.

"Permanent magnets" and "permanent magnet materials" herein refer to anisotropic or "oriented" materials which have a preferred magnetization axis. When these materials are magnetized, they produce magnetic fields that are always "on".

"Ferromagnetic poles," "soft ferromagnetic poles," "pole(s)" and "pole pieces" as used herein refer to pieces or members, of any shape, made from soft ferromagnetic materials. Soft ferromagnetic materials are macroscopically isotropic or non-oriented. When these materials have not been exposed to an external magnetic field they produce no magnetic field of their own.

"Hybrid magnets" or "hybrid magnetic structures" as used herein refers to devices having a combination of permanent magnet material and soft ferromagnetic pole pieces, wherein the soft ferromagnetic pole pieces alternate in a periodic array with blocks of permanent magnet material. The magnetic fields of each block of permanent magnet material are oriented orthogonal to a lateral plane of the soft ferromagnetic poles and in the opposite direction of each adjacent block of permanent magnet material. In one view of the hybrid magnetic structure whereby the tip of the ferromagnetic pole extends beyond the blocks of permanent magnet material and the blocks of permanent magnet material extend below the bottom edge of the ferromagnetic pole.

"Hybrid magnet(ic) tweezers" as used herein refers to a multi-pole hybrid magnetic structure. For example, the hybrid magnetic tweezers may be comprised of mirror image hybrid magnetic structures, a dipole hybrid magnetic structure, or a single pole hybrid magnetic structure having an aperture through the pole.

"Magnetization orientation," "anisotropic orientation" or "magnet(ic) orientation" as used herein refers to the magnetic orientation or a preferred magnetization axis of permanent magnet material.

"Field" or "field level" as used herein refers to the magnetic fields generated by the ferromagnetic and permanent magnet materials in the magnet structure. Fields are expressed in units of Gauss (G) or Tesla (T).

"High field(s)" as used herein refers to the magnetic fields generated above 0.6 Tesla or 6000 Gauss.

"Field gradient structure" as used herein refers to the shape of the magnetic field gradient produced by controlling the shape, size and number of ferromagnetic poles and the quantity and vertical dimension of the permanent magnet materials used in the hybrid magnetic structure.

"Geometric periodicity" as used herein refers to the distance or length over which the geometric pattern is repeated, specifically, the distance or length over which the geometric pattern of ferromagnetic poles and blocks of permanent magnet material is repeated. For example, the geometric periodicity of a preferred embodiment can be measured as the distance between the center of a first ferromagnetic pole tip and the center of the next adjacent pole tip or from the leading edge of a first ferromagnetic pole tip to the leading edge of the next adjacent pole tip.

"Magnetic Periodicity" refers to the periodic magnetic field created at the ferromagnetic pole tips and is typically twice the geometric period length.

"Microtiter plates" as used herein refers to industry-standard plastic plates that conform to a standard footprint size and that incorporate 96, 384 or 1536 wells that act as containers for various biological and chemical solutions. Microtiter plates are 8×12 arrays of 96 wells, 16×24 arrays of 384 wells and 32×48 arrays of 1536 wells. Microtiter plates that are used with magnet structures include "PCR" plates, that are made of materials such as polystyrene and have conically-shaped wells, and other available round or flat bottom well plates or blocks that are used as liquid containment vessels in biological applications.

"Orthogonal" as used herein refers to an orientation of about 90° in any direction from the reference angle or perpendicular at right angles.

"Blocks" as used herein refers to any desired shape of material including but not limited to, annular or partially annular, cylindrical, toroidal, helical, a triangular prism, a quadrangular prism, a hexagonal prism or any other polyhedron, T-shaped, and inverted L-shaped. These "blocks" have a cross-sectional area. Examples of preferred cross-sectional shapes include but are not limited to, square, rectangle, circle, elliptical, wedge, triangle, quadrilateral, and other polygons.

"Rare earth magnets" as used herein refer to permanent magnetic materials containing any of the rare earth elements (Elements 39, 57-71) such as neodymium or samarium.

"Target" as used herein refers to magnetized molecules, particles or bodies including but not limited to proteins, polymers, nucleic acids, peptides, DNA, RNA, entire cells and other cellular particles; and to magnetized particles or bodies of nano, micro or larger size, beads and particles made of materials including but not limited to metals, semiconductor materials, glass, ceramic and rubber.

Introduction

The present invention provides hybrid magnetic structure comprised of mirror image single pole hybrid magnetic structures made from a combination of permanent magnets and ferromagnetic materials. In the present invention, the hybrid magnetic structures can be used to make single pole and dipole hybrid magnetic tweezers and flow separators which are useful for manipulation or separation of magnetizable molecular structures and targets. The hybrid magnetic structure is applicable to work in the broader fields of functional genomics and proteomics since it can be used for selective separation of molecular particles from cellular and other matter. In addition, the structure can be used in high-throughput drug development and other industrial processes requiring magnetic manipulation of dense arrays of samples in solution. A primary performance goal of these magnetic structures is to create a field distribution in a small volume that exhibits high magnetic flux density and a strong gradient.

The combination of permanent magnet material and ferromagnetic poles creates a high flux density magnetic field in the pole material. Further shaping of the poles conveys the high magnetic flux to the region of application and creates a strong gradient field distribution in that region. This defining characteristic allows the hybrid magnetic structure to produce fields and gradients that are up to four times greater than previous magnet structures and a more beneficial field distribution for a number of important applications.

A. Components and Materials of the Hybrid Magnetic Structure for Hybrid Magnetic Tweezers To achieve the desired field characteristics, a preferred embodiment of the hybrid magnetic structure would utilize a three-stage flux concentrating mechanism described herein. Referring now to FIG. 1A, the hybrid magnetic structure 100 is comprised of a ferromagnetic pole 120 located between permanent magnet blocks 140 whose magnetization orientations 170 have a significant component orthogonal to the contact surface of the ferromagnetic pole 120 and which overhang the back edge of the pole. The ferromagnetic pole 120 has a shaped tip 130 extending away from the permanent magnet material in the direction of the region of interest 180 and transports magnetic flux out of the hybrid structure while maintaining concentration of the flux. In a preferred embodiment, the ferromagnetic pole tip 130 preferably contains a notch or concavity 135 at the very tip of the pole that directs and further concentrates or reduces divergence of the magnetic flux in the region of interest immediately beyond the pole 120 and outside the material of the pole into the region of interest 180.

Figure 1B:
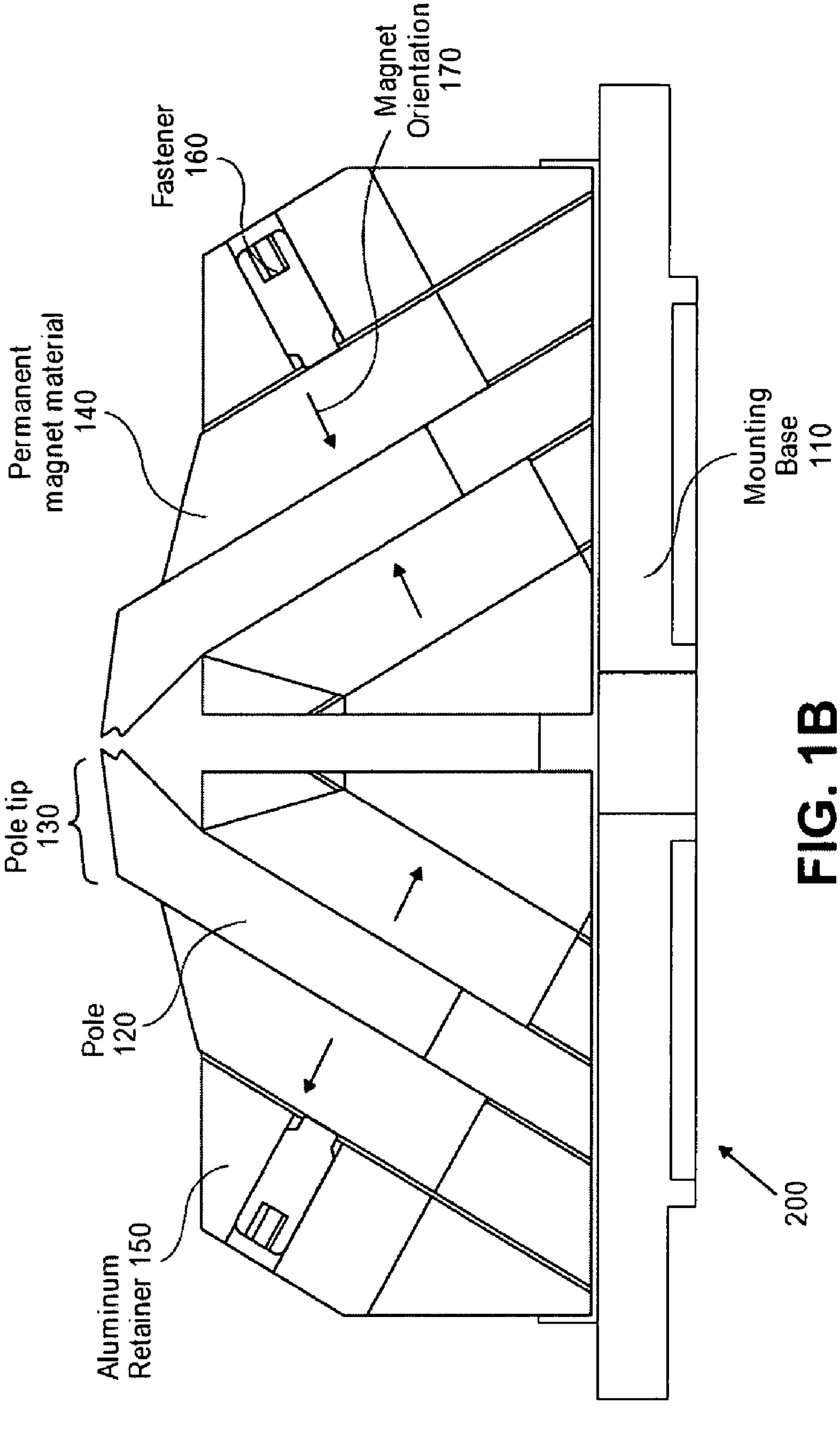
FIG. 1B is a cross-sectional view of the hybrid magnetic tweezers comprised of the hybrid magnetic structures. The pole pieces of two identical hybrid magnetic structure in mirror symmetry ate separated by 0.8 mm. The gap can be adjusted in a continuous or discrete manner.

Referring now to FIG. 1B, the component parts of the core assembly of a preferred embodiment of the hybrid magnetic tweezers 200 generally comprise paired mirror image hybrid magnetic structures 100, wherein each hybrid magnetic structure comprises a non-magnetic base 110; a shaped ferromagnetic pole 120 having wedge-shaped tip 130 featuring a notch or concavity 135; and blocks of permanent magnet material 140.

In another preferred embodiment, the core assembly is comprised of a hybrid magnetic structure comprising a non-magnetic base 110; a ferromagnetic pole 120; a ferromagnetic pole 120 having a shaped tip 130 featuring a notch or concavity 135; and blocks of permanent magnet material 140.

Figure 2A:
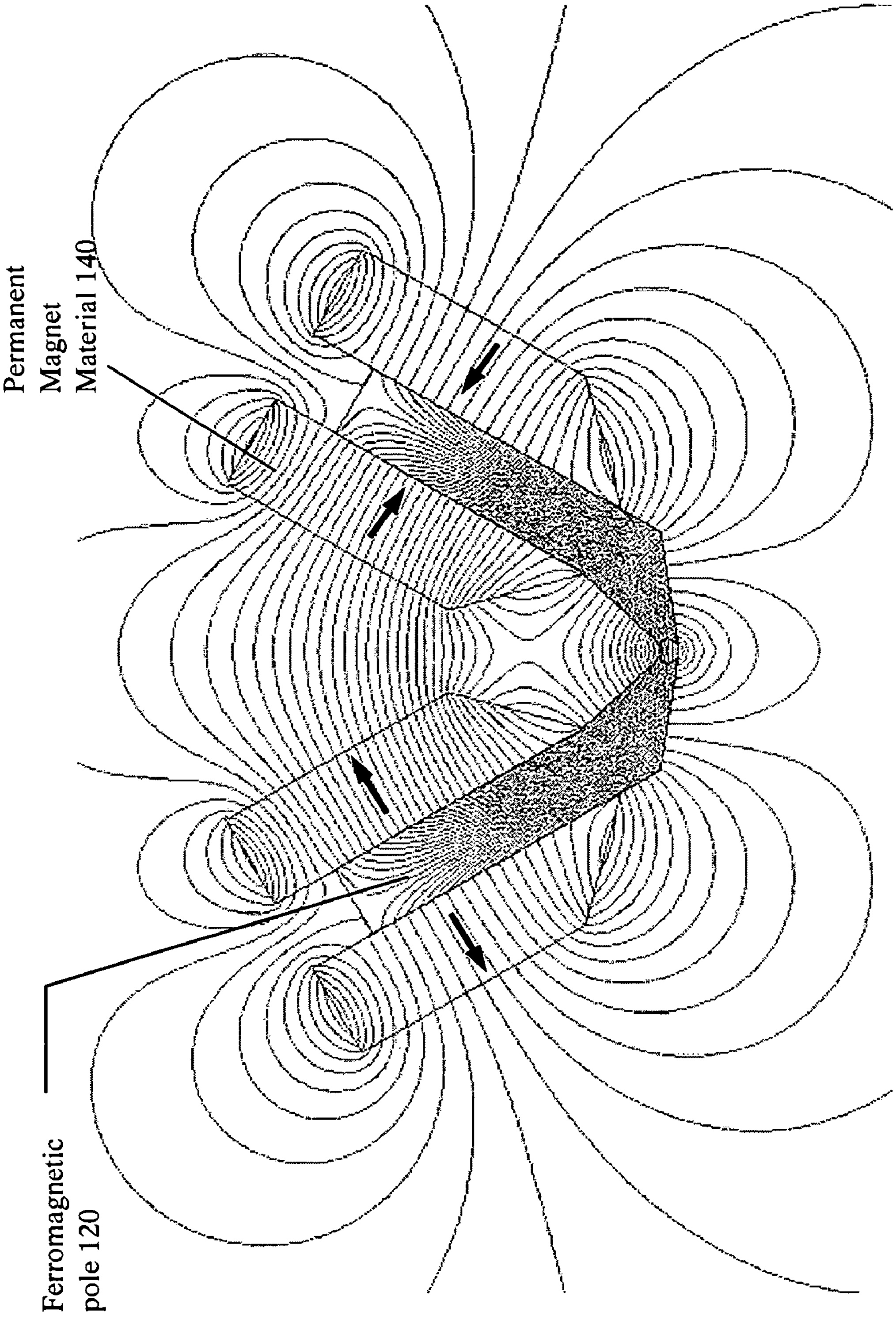
FIG. 2A is a schematic showing the field lines obtained by 2D simulation for a slice through the dual asymmetric pole hybrid magnetic structure in FIG. 1A.

The hybrid magnetic structures are preferably comprised as follows. A ferromagnetic pole 120 is assembled onto the base 110 adjacent to a block of permanent magnet material 130. In some embodiments, the blocks of permanent magnet material 140 and the ferromagnetic pole 120 are in a periodic array. The magnetic orientations 170 of each block of permanent magnet material are orthogonal to a lateral plane of the ferromagnetic poles 120, and in the opposite direction to that of each adjacent block of permanent magnet material 140. (FIG. 1A). In other embodiments, the hybrid magnetic structures are comprised of monopole, di-pole or multi-pole structures, such as those shown in FIGS. 2, 3, and 4, wherein the assembled ferromagnetic poles 120 and blocks of permanent magnet material 140 are symmetrical, asymmetrical, parallel or opposite one another. In a preferred embodiment, the base 110 holds the multiple hybrid magnetic structures of the hybrid magnetic tweezers together as one monolithic structure 200 as shown in FIG. 1B.

The tip 130 of the ferromagnetic pole 120 should extend beyond the blocks of permanent magnet material 140. The block of permanent magnet material 140 should extend beyond the bottom edge of the ferromagnetic pole 132. A cross section of a preferred embodiment of the hybrid magnetic structure is shown with magnet orientations in FIG. 1B.

A preferred embodiment can further comprise a means for holding the base 110, ferromagnetic pole 120 and blocks of permanent magnet material 140 together by means of retainer 150 for the outboard magnets or a high strength bonding agent to hold components together. The retainer 150 and the non-magnetic base 110 would act as restraining mechanisms.

The soft ferromagnetic poles 120 and the shaped ferromagnetic pole tips 130 can be fashioned from soft ferromagnetic material such as steel, low-carbon steel, vanadium pemendur, or other high-permeability magnetic material.

The ferromagnetic pole tip 130 can be angled or bent relative to the ferromagnetic pole such as the ferromagnetic pole tips in FIGS. 1A, 2, 3 and 4. It is contemplated that the angle can be from 0 to up to at least 90 degrees such that the tip is orthogonal to the pole 120. In a preferred embodiment, the tip angle is about 45 degrees such that a region of interest between the pole tips is created by pairing the hybrid magnetic structure having a ferromagnetic pole with an angled tip with a second hybrid magnetic structure. In a preferred embodiment, the second hybrid magnetic structure is in mirror symmetry of the first hybrid magnetic structure.

Figure 2B:
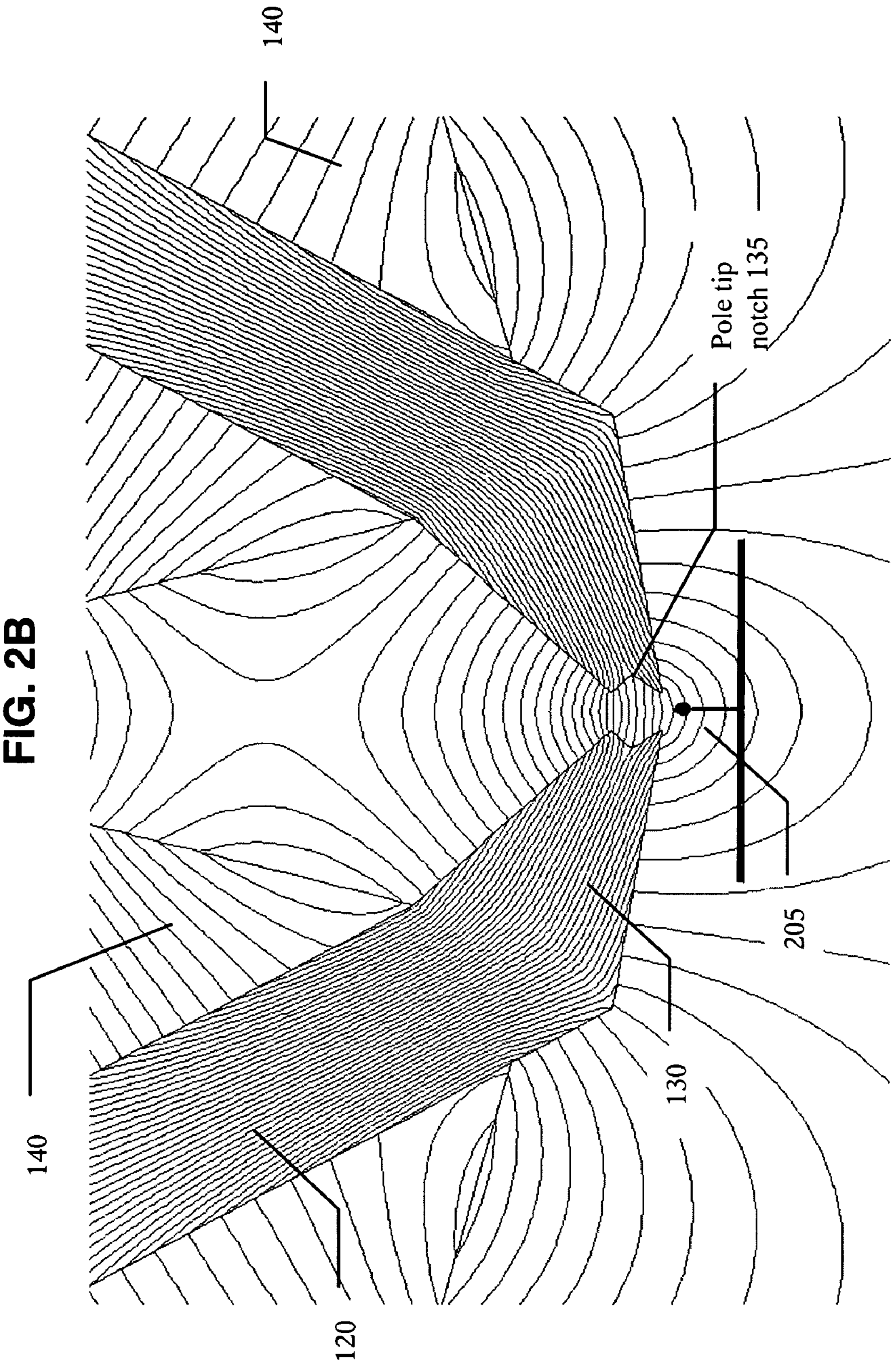
FIG. 2B shows a close-up view of the field lines through the 45 degree angle pole tips and the region of interest where a magnetized target is attached to a substrate. Target and bead are not to scale.
Figure 3A:
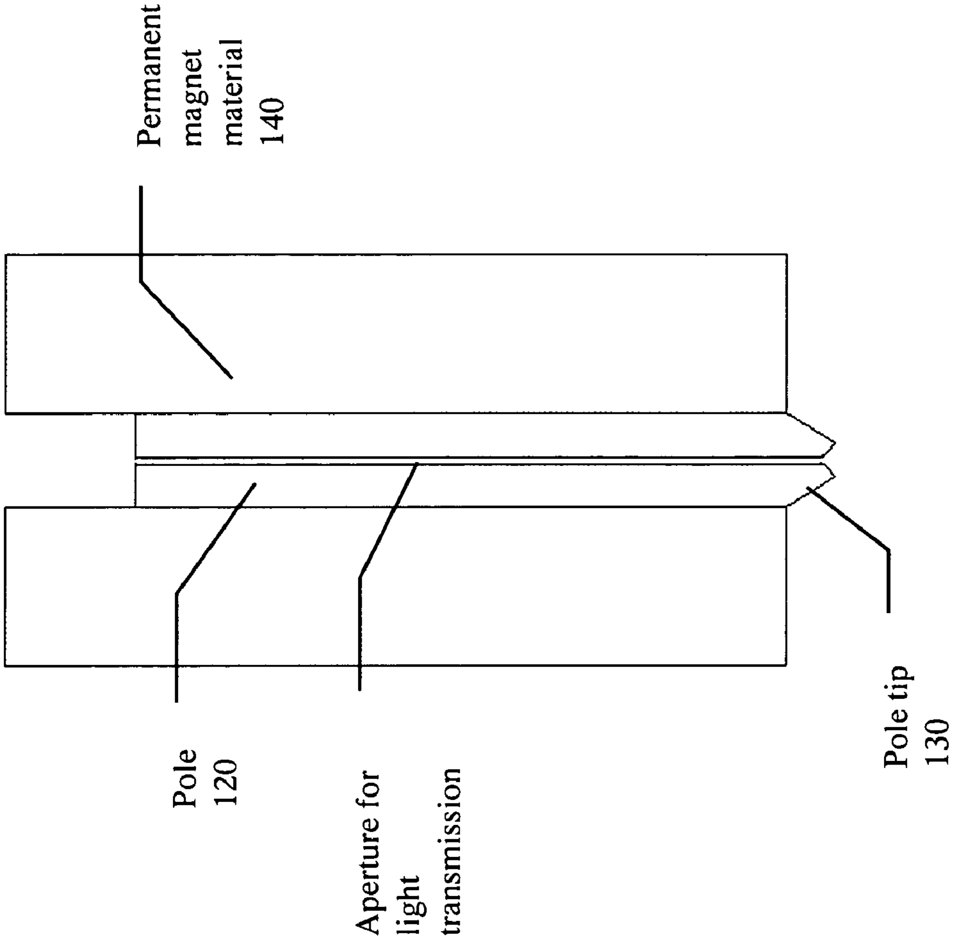
FIG. 3A is a cross-sectional view of a single pole hybrid magnetic structure having a light aperture through the center of the pole.

Referring to FIG. 2B, in a preferred embodiment, the ferromagnetic pole tip 130 features a notch or concavity to create a discrete region of interest just above and inside the notch and concavity. The notch or concavity 135 also creates high fields in the region of interest 180. In a preferred embodiment, the concavity would have a curvature that is three-dimensional. For example, the concavity can be cup-shaped. In some embodiments, the concavity is two-dimensional and in other embodiments, a notch is used. The notch or concavity

135 in the pole tip 130 can be made by conventional machining methods. The radius or depth of the notch can vary according to the strength and the shape of the desired fields. In a preferred embodiment, the pole tip concavity is a notch 135 up to 0.5 mm into the tip 130.

Figure 3B:
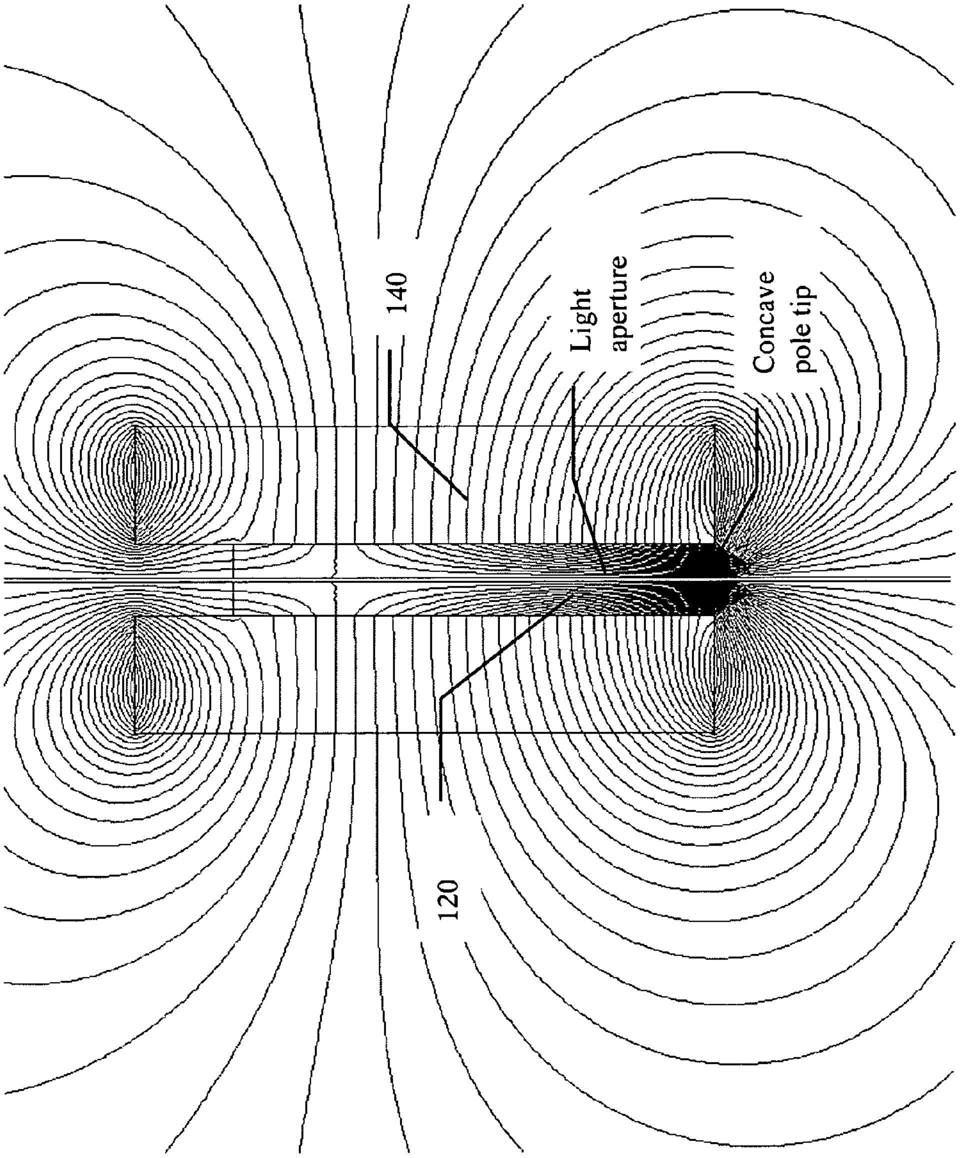
FIG. 3B is a schematic showing the field lines obtained by 2D simulation for a slice through the single pole hybrid magnetic structure in FIG. 3A. Shown in FIG. 3B but not in 3A is the ferromagnetic shim inserted between permanent magnet blocks.

In another embodiment, ferromagnetic pole 120 has a hole through the pole to allow a light source to illuminate through the pole (FIG. 3). The diameter of the aperture should ideally be smaller than the pole tip width at the slimmest portion of the pole tip 130. In a preferred embodiment, the hole through the pole should have a radius or diameter size sufficient for a capillary or optical fiber to fit through or clearance for a fiber optic conduit. In another embodiment, the hole is a simple aperture for light source to reach the molecular target.

Air gaps between the pole tips can reduce the field strength. Thus, it is important to use materials that will not dissipate the field strength or reduce it. For example, in an embodiment having two parallel hybrid magnetic structures forming a structure shown in FIG. 4B, where there is a gap between the poles 120 and the pole tips 130 at the point of interest 180, inserting a ferromagnetic shim 145 made of high permeability magnet steel in the air gap will not appreciably reduce the field strength. In such an embodiment, the gap can be adjusted by inserting the correct thickness of shim 145. In another embodiment, the gap between the hybrid magnetic structures can be adjusted by manual means or motor. Gap adjustment can also be between pole tips 130, between the pole tip and distance gap between a magnetic bead attached to a molecule of interest.

Figure 6A:
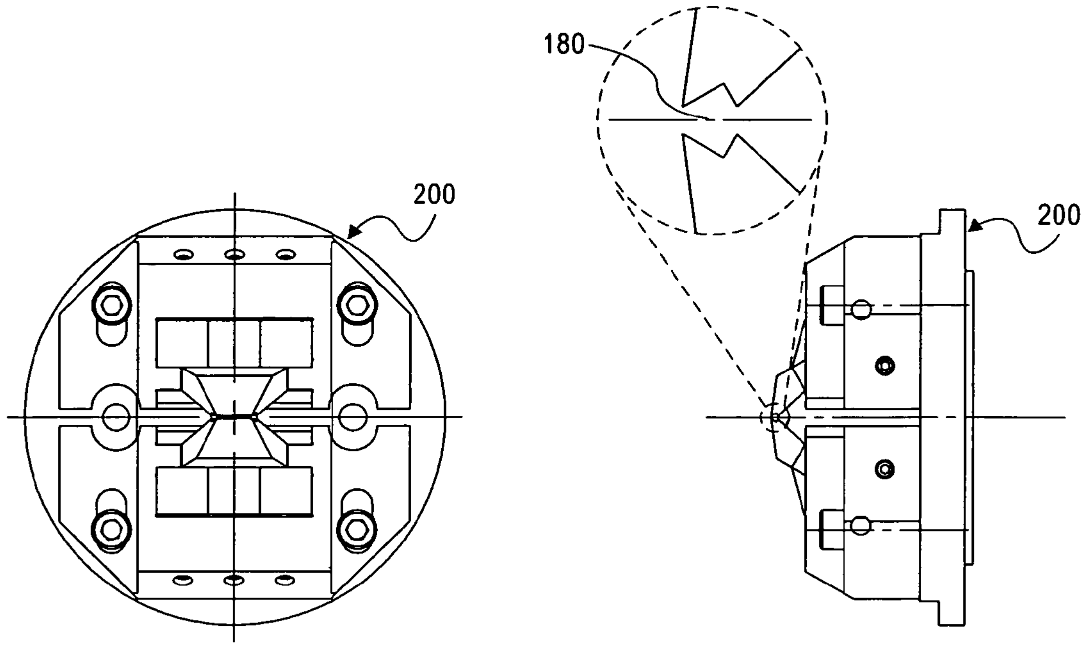
FIG. 6A shows a top view of the hybrid asymmetric dipole magnetic tweezers assembly and cross-sectional view of the assembly with a magnified view of the pole tip region of interest.
Figure 6B:
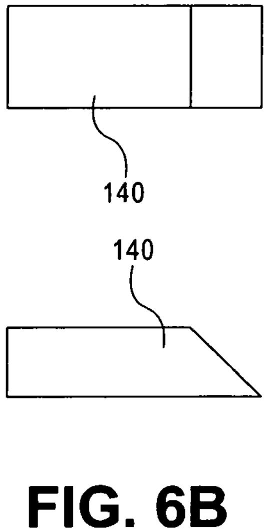
FIG. 6B shows a top and side view of the permanent magnet block.
Figure 6C:
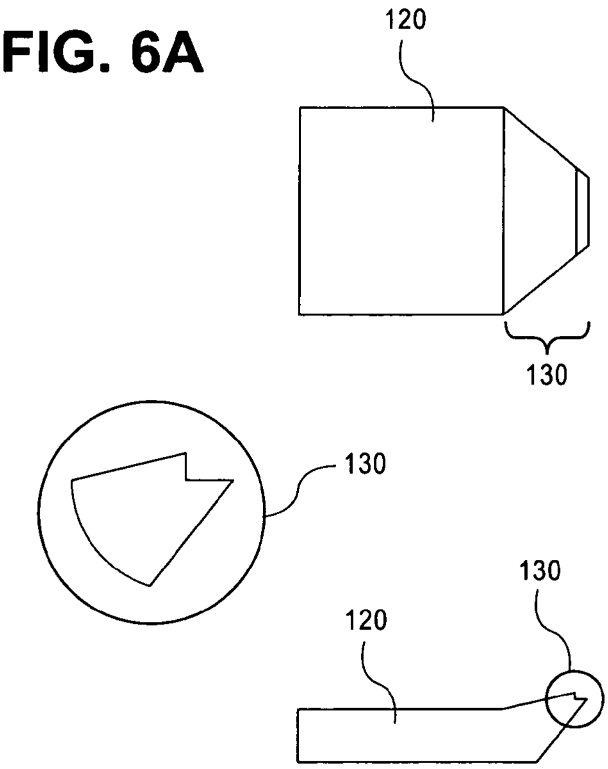
FIG. 6C shows a top and side view of the pole and a magnified view of the pole tip.

Permanent magnet materials 140 that are suitable for use in this invention are any oriented high field rare-earth materials and non-rare-earth materials such as hard-ferrites. Examples of preferred materials include, but are not limited to, rare-earth magnet materials, such as neodymium-iron-boron or samarium cobalt. An example of a permanent magnet block is shown in two views in FIG. 6B.

In a preferred embodiment, there are at least two blocks of permanent magnet material 140 placed adjacent to the ferromagnetic pole on two opposing sides of the pole with the magnetization orientations in opposing directions. In another embodiment, there are more than two blocks of permanent magnet material placed adjacent to the ferromagnetic pole. In such an embodiment, the direction of the magnetization orientations of each block of permanent magnet material should all point either into the ferromagnetic pole or out of the ferromagnetic pole. In one embodiment, the blocks of permanent magnet material can be rectangular blocks, or in other embodiments, angled at the edges closest to the ferromagnetic pole tips.

Figure 6D:
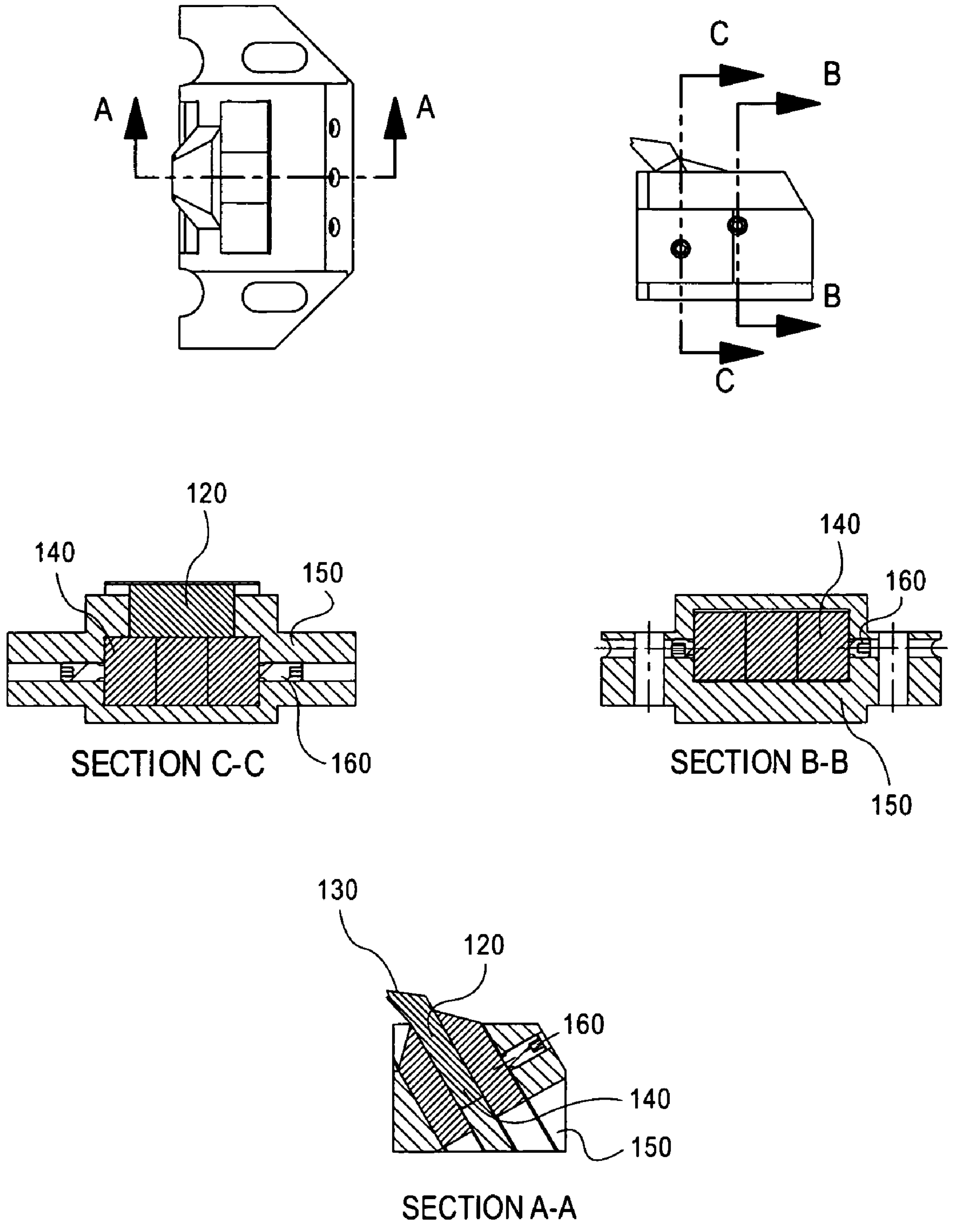
FIG. 6D shows cross-sectional views A-A, B-B and C-C of the retainer hybrid asymmetric dipole magnetic tweezers assembly.
Figure 6E:
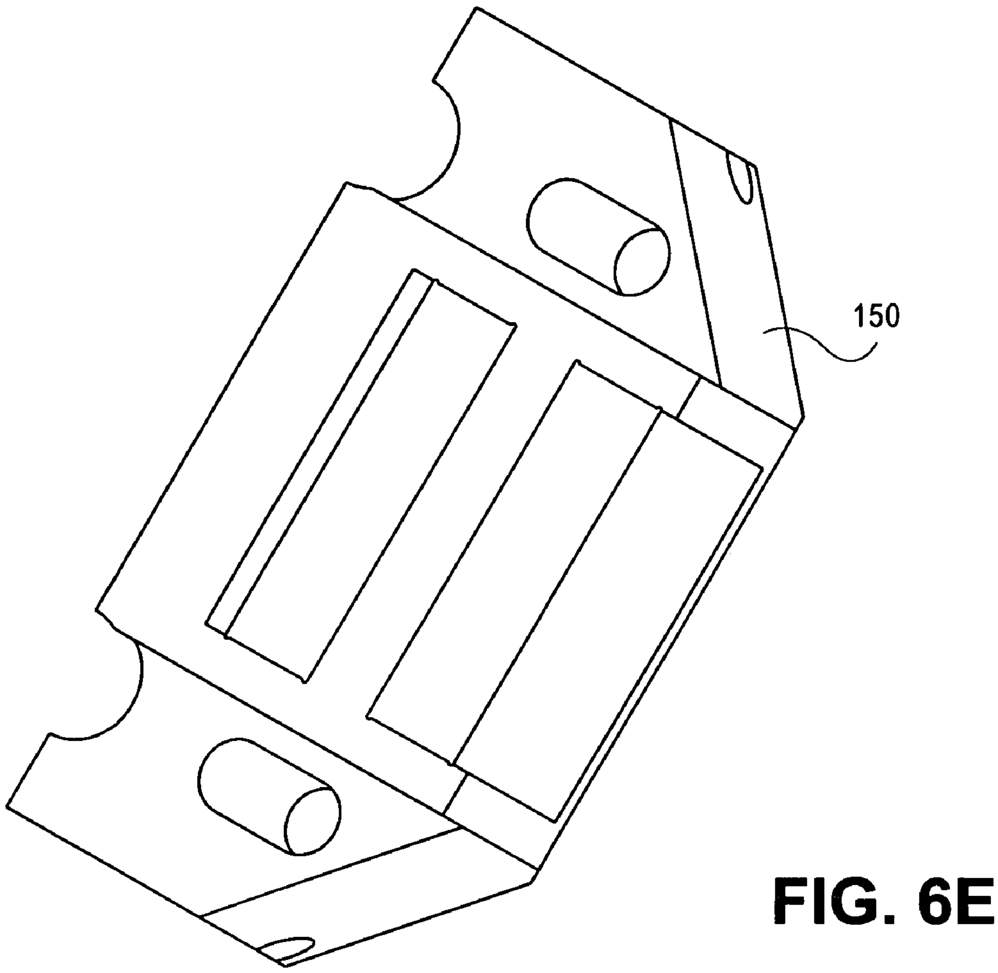
FIGS. 6E-K show varying views of the retainer.
Figure 6F:
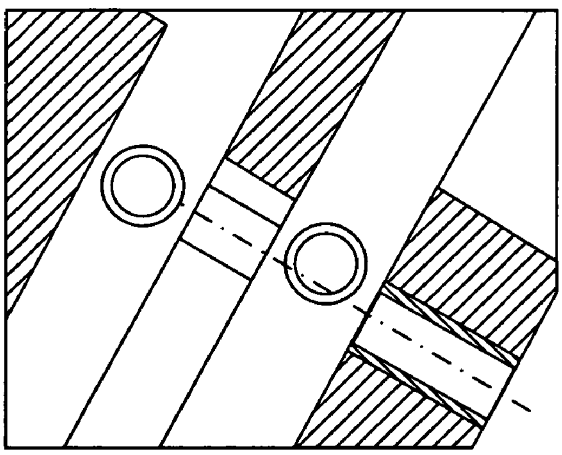
Figure 6G:
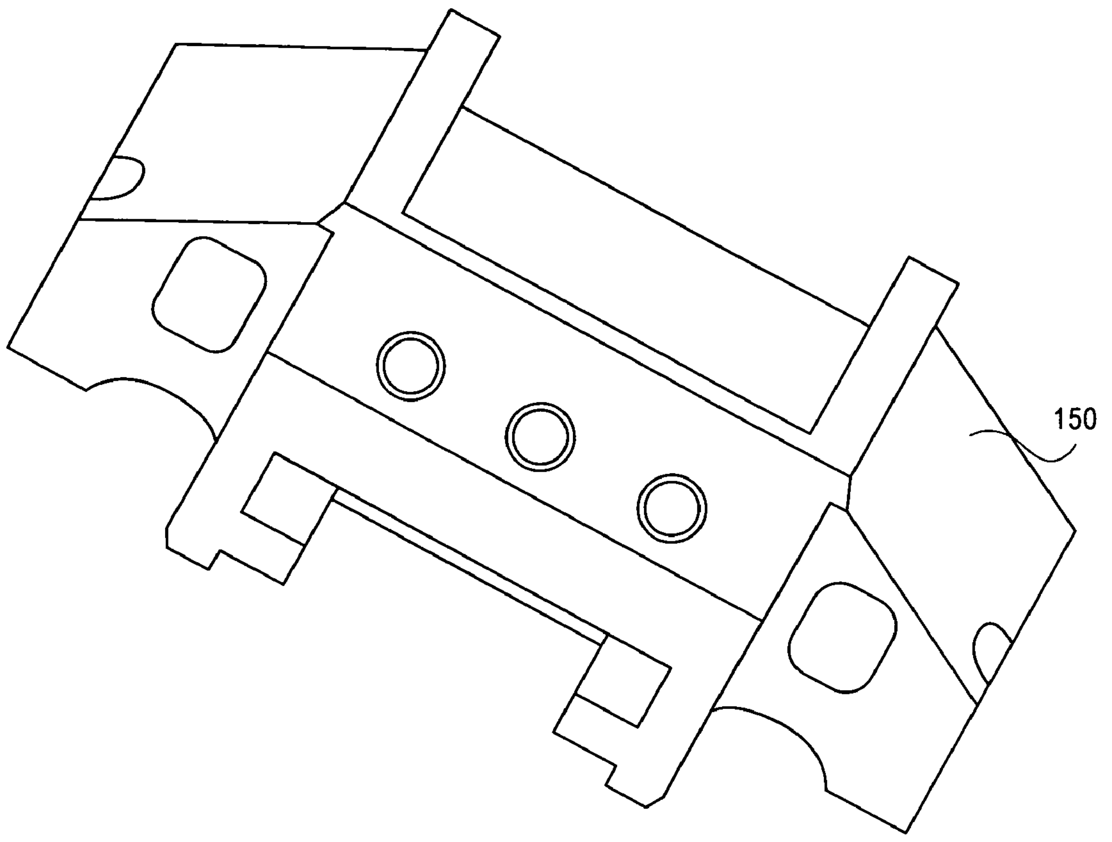
Figure 6H:
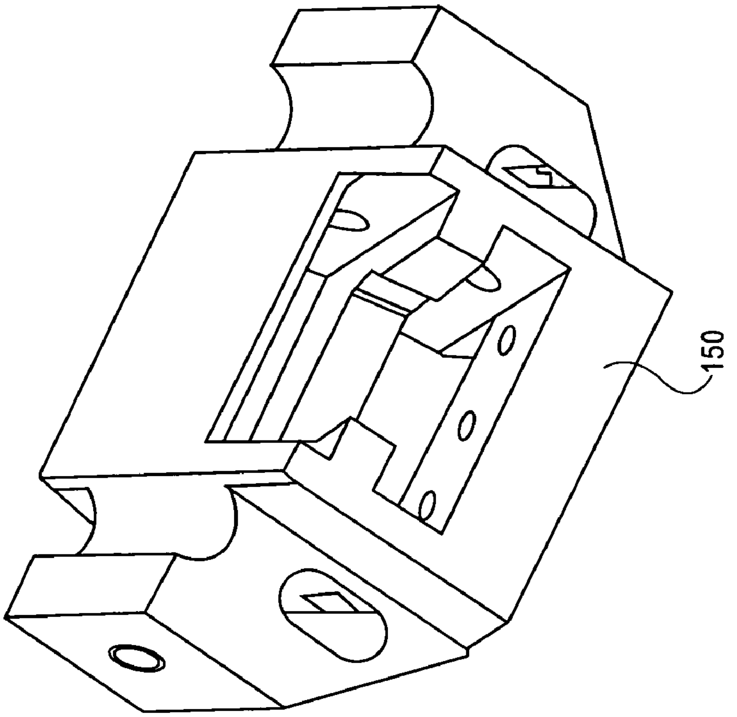
Figure 6H:
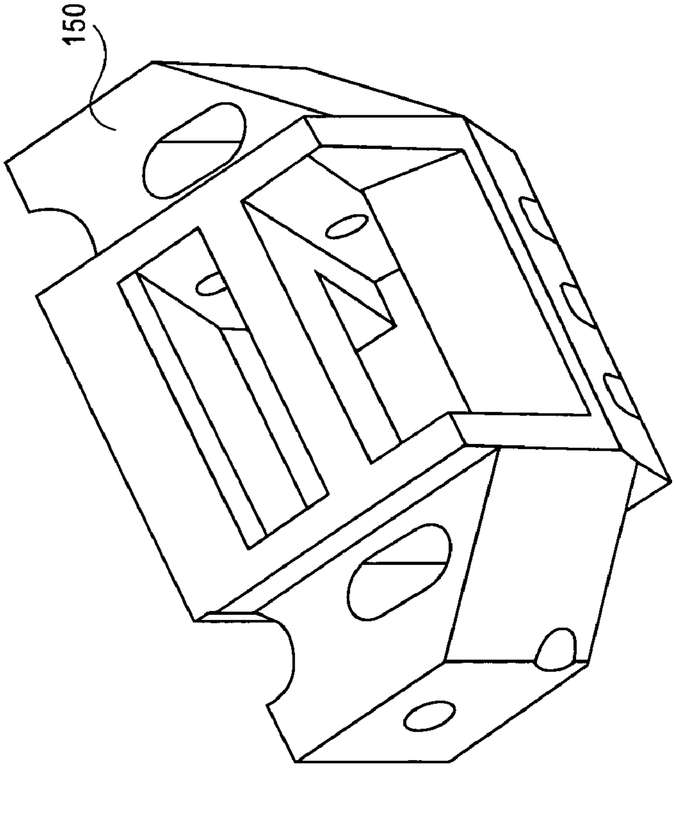
Figure 6I:
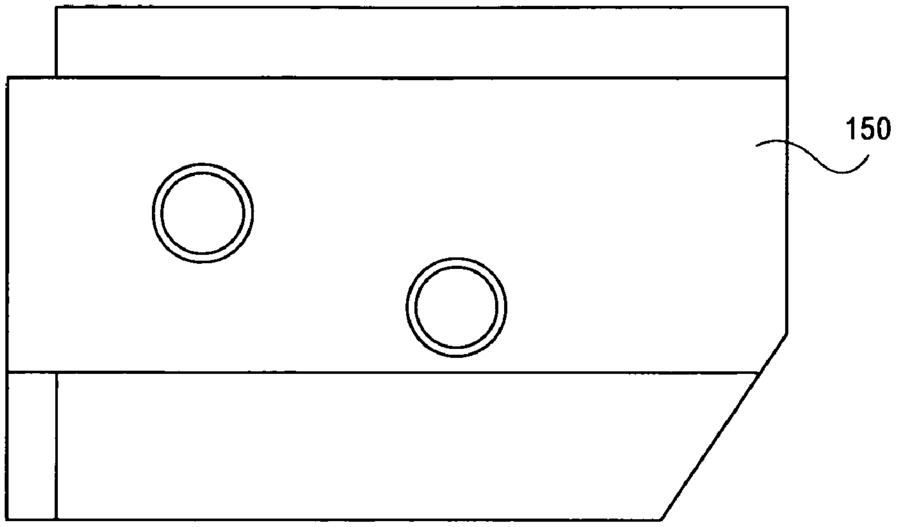
Figure 6J:
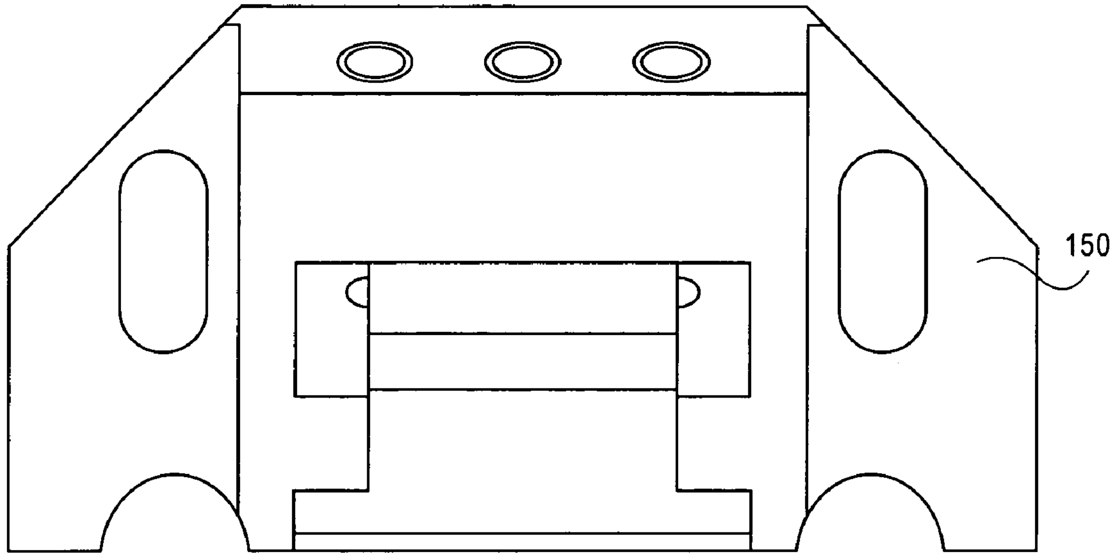
Figure 6K:
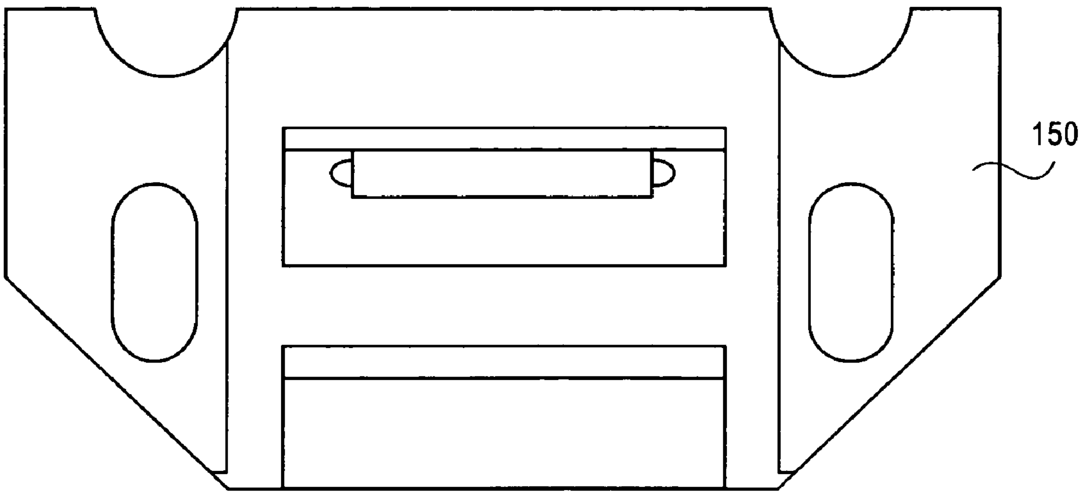
Figure 6K:
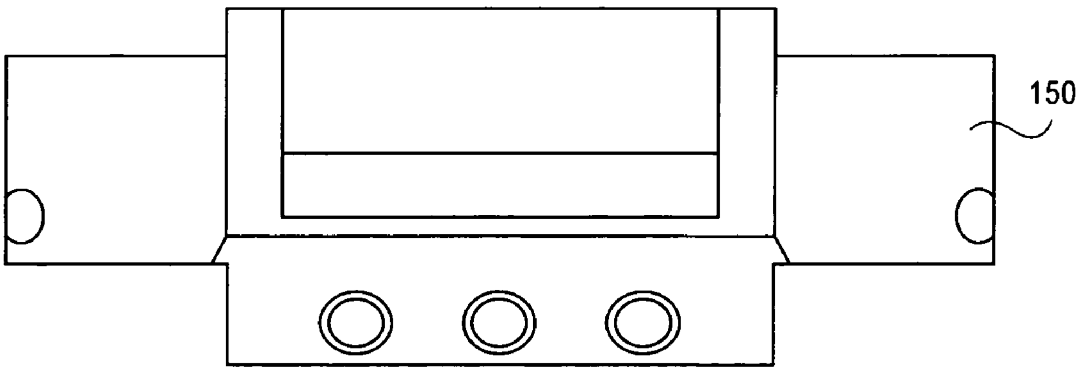
Figure 6L:
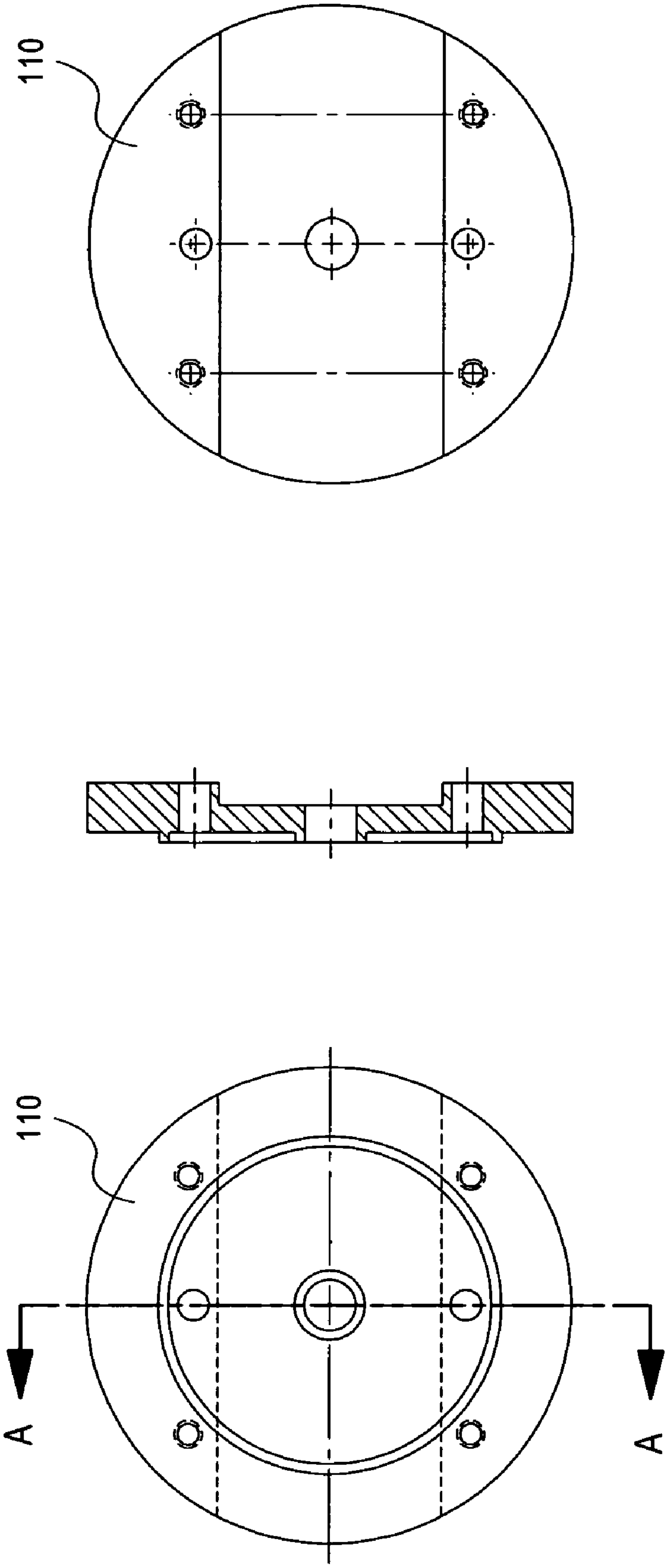
FIG. 6L shows a top view, a cross-sectional view and a bottom view of the mounting plate.

The non-magnetic base means 110 can be made from any non-magnetic metal, high-strength composite or other non-magnetic material having sufficient mechanical properties, but preferably a material that is rigid, light and can be easily machined or molded. Examples of such suitable non-magnetic materials are: aluminum, a composite or plastic. Schematics for a non-magnetic base are shown in FIG. 6L.

A non-magnetic base is recited and preferred, however, some embodiments may require a base comprised of ferromagnetic materials to be used as a shield to redirect stray magnetic fields away from the base. For example, if there is sensitive circuitry below the area whereupon the hybrid magnetic structure is placed, a base comprised of ferromagnetic materials should be used to redirect the magnetic fields up and away from the circuitry.

In another embodiment, non-magnetic spacers may also be required to fill in overhangs or empty spaces on the sides or ends of the poles and/or permanent magnet blocks.

The performance of the hybrid magnetic structure 100 and the hybrid magnetic tweezers 200 is not dependent on a particular material but on the magnetic geometry and design. Materials can be exchanged and modified based on what kind of performance or cost parameters are set. Commercially available material can be ordered from industry vendors according to a specified shape and size.

A person skilled in the art would appreciate that these structures experience high-magnitude internal forces during and after assembly and require a means for holding the base, pole pieces and permanent magnet material together. Referring to FIGS. 5A-D, it is preferred that a retainer and base system be fashioned as the means for holding the base 110, the ferromagnetic pole(s) 120 and the blocks of high field permanent magnet material 140 together, from non-magnetic metal or high-strength composite. In a preferred embodiment, the retainers 150 are also preferably held to the base by means of fasteners 160. These fasteners 160 are generally non-magnetic stainless steel or other corrosion resistant material with similar mechanical characteristics. Referring to FIG. 6D, in a preferred embodiment, the retainer 150 is a single monolithic piece holding the hybrid magnetic structure 100 to the base 110. A preferred example of a retainer 150 is shown in various views in detail in FIGS. 6C-6K.

The hybrid magnetic structure, retainer and base are made by machining the component parts and then assembled usually by means of clamping fixtures and secured by means for holding the base, ferromagnetic pole and blocks of high field permanent magnet material together, preferably through the design of retainers and use of high strength bonding agent. The hybrid magnetic structure components are preferably bonded together because the internal forces are strong. Preferable bonding agents for application in this invention include unfilled epoxies having cured strengths greater than or equal to 2000 pounds per square inch.

Figure 1C:
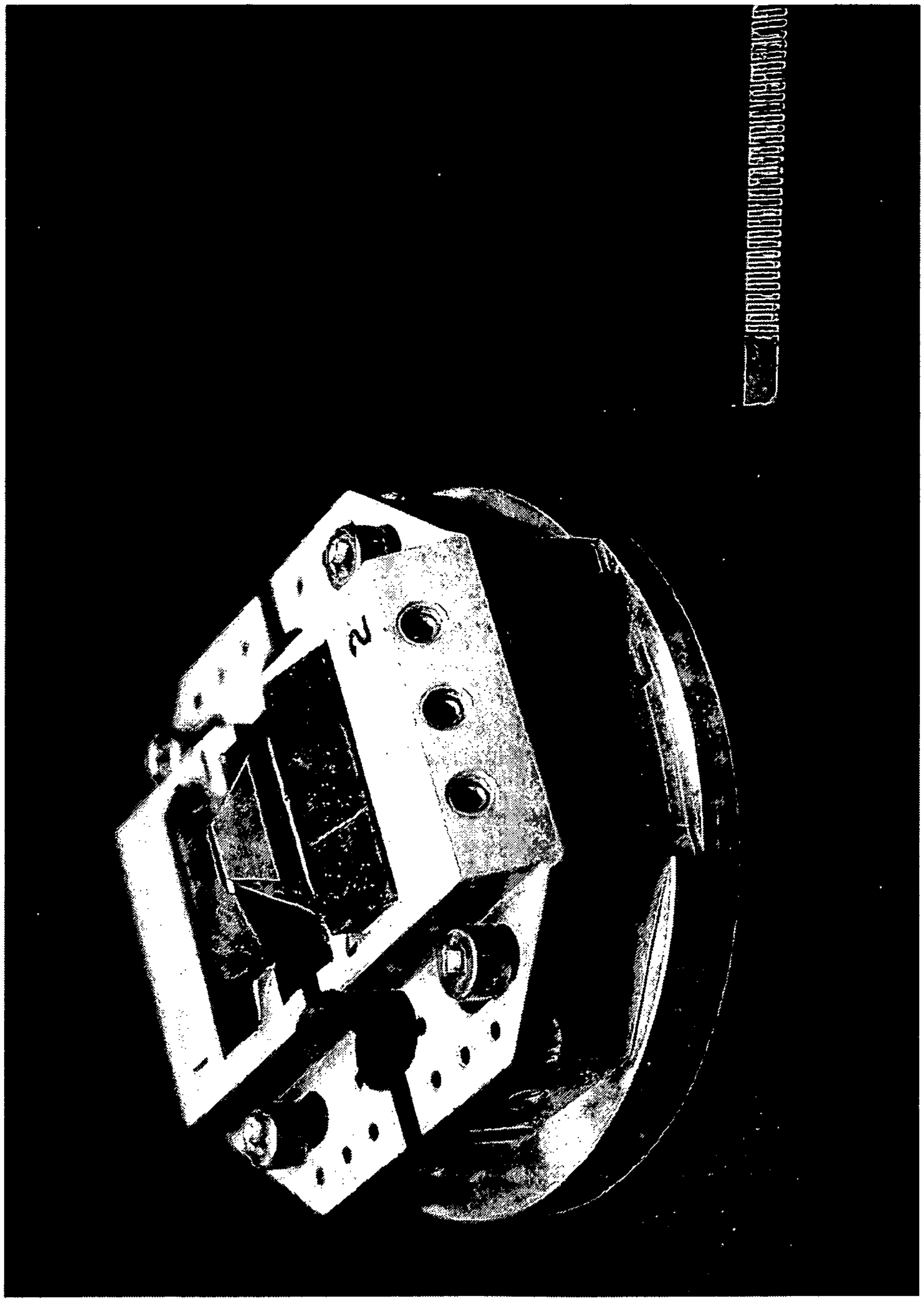
FIG. 1C is a photograph of the hybrid magnetic tweezers next to a ruler to compare size. The bar indicates 1 cm.

Furthermore, because of the high field strengths of the magnetic structure's components, a system of bonding and clamping fixtures may be designed that allows for efficient and rapid fabrication of these devices. Examples of methods for assembling hybrid magnetic structures are described in issued U.S. Pat. No. 6,954,128. A method for assembling a preferred hybrid magnetic tweezers in FIG. 5 is described in Example 1. Total dimensions for hybrid magnetic tweezers assembly in a preferred embodiment are shown with the comparison of the assembly with a ruler in FIG. 1C.

In one embodiment, the retainer and base systems have positions for insertion of pins such as clavel pins, which allow for precise location; slotted holes for gap adjustment between the poles; and holes for pushers screws to hold the structure together.

The dimensions of the hybrid magnetic structure vary with the particular specialized application of the hybrid magnetic tweezers. Therefore, the exact dimensions and configurations of the hybrid magnetic structure and the magnetic flux potentials are all considered to be within the knowledge of persons conversant with this art. It is therefore considered that the foregoing disclosure relates to a general illustration of the invention and should not be construed in any limiting sense.

B. Magnetic circuit and Gradient Distributions (1) Magnetic Circuit

A feature of this hybrid magnetic structure is that the field strength can be increased by increasing the height of the permanent magnet material and the ferromagnetic poles. The hybrid magnetic structure is stand-alone and requires no external power source. It is powered solely by the magnetic circuit created by the permanent magnet material and the soft ferromagnetic poles.

As the height of the structure is increased, as in the case where the height of the poles from the bottom edge to the tip is increased, the flux density in the pole tips increases up to the limiting case where the pole tips reach their saturation point. For common magnet steels this saturation point is at approximately 17 kilo-Gauss. The implications are that the utilizable field levels for these magnetic structures can be close to that of saturation field level. In addition, because of the saturation condition in the magnet poles, the field gradients external to the pole tips (and hence, the forces on magnetized particles) can be very strong.

As shown in FIG. 1A, the permanent magnet material 140 is assembled with the magnetization orientation orthogonal to a lateral plane of the ferromagnetic poles and in opposing directions, to create a large pole-to-pole scalar potential difference that results in high magnetic flux density between the upper pole tips and a corresponding, alternating polarity.

The permanent magnet material 140 should extend below the bottom edges 132 of the soft ferromagnetic poles 120. In one embodiment, grooves can be machined into the base 110. The permanent magnet material 140 that extends below the bottom edge 132 of the poles 120 inhibits the pole-to-pole flux and results in a reduced field at the lower surfaces of the magnetic structure. As such, it is important to incorporate this aspect of the hybrid magnetic structure into its design if the application uses mainly the upper surface of the structure.

(2) Computer Modeling

One skilled in the art would appreciate the use of three dimensional computer models to further develop and quantify the performance of these magnetic structures. A suitable computer program is used to calculate and determine what the field distributions should be, while taking into account the materials and geometry that will be employed. The AMPERES code is available from Integrated Engineering Software, *AMPERES, Three-dimensional Magnetic Field Solver*, (Winnipeg, Manitoba, Canada). Suitable programs, in addition to AMPERES, include, but are not limited to, TOSCA (made by Vector Fields Inc., Aurora, Ill.), ANSYS (ANSYS, Inc., Canonsburg, Pa.), POISSON, PANDIRA and POISSON SUPERFISH 2-D (Los Alamos Accelerator Code Group (LAACG), Los Alamos National Laboratory, Los Alamos, N. Mex.).

Use of this software can be used to construct and solve hybrid magnetic structure boundary element models (BEM) that incorporate all significant geometric attributes and non-linear behavior of isotropic, ferromagnetic steel, verify the fields that will be created, and mathematically evaluate the magnetic performance of the proposed model and all attributes of the fields that will be generated by the proposed model.

Those skilled in the art would appreciate that in order to perform secondary two-dimensional field calculations such as solving the field gradient problem or the force experienced by magnetized targets in the field, it is useful to start by obtaining the vector potential solution of a boundary value numerical model of the hybrid magnetic structure. After finding a numerical solution for the vector potential, then post-processing computations can be performed to find the field values and associated derived quantities.

Figure 4A:
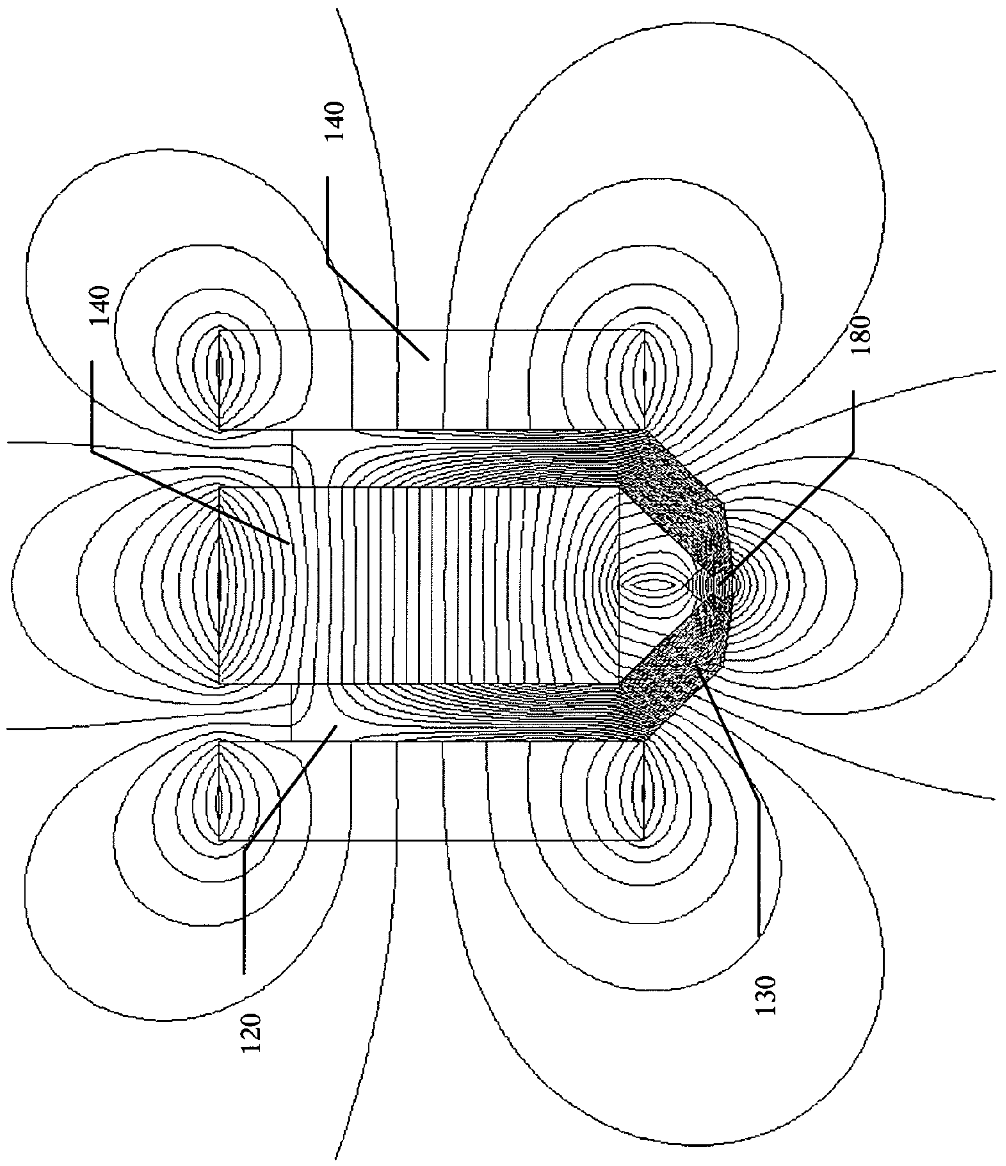
FIG. 4A is a schematic showing the field lines obtained by 2D simulation for a slice through the dual parallel pole hybrid magnetic structure.
Figure 4B:
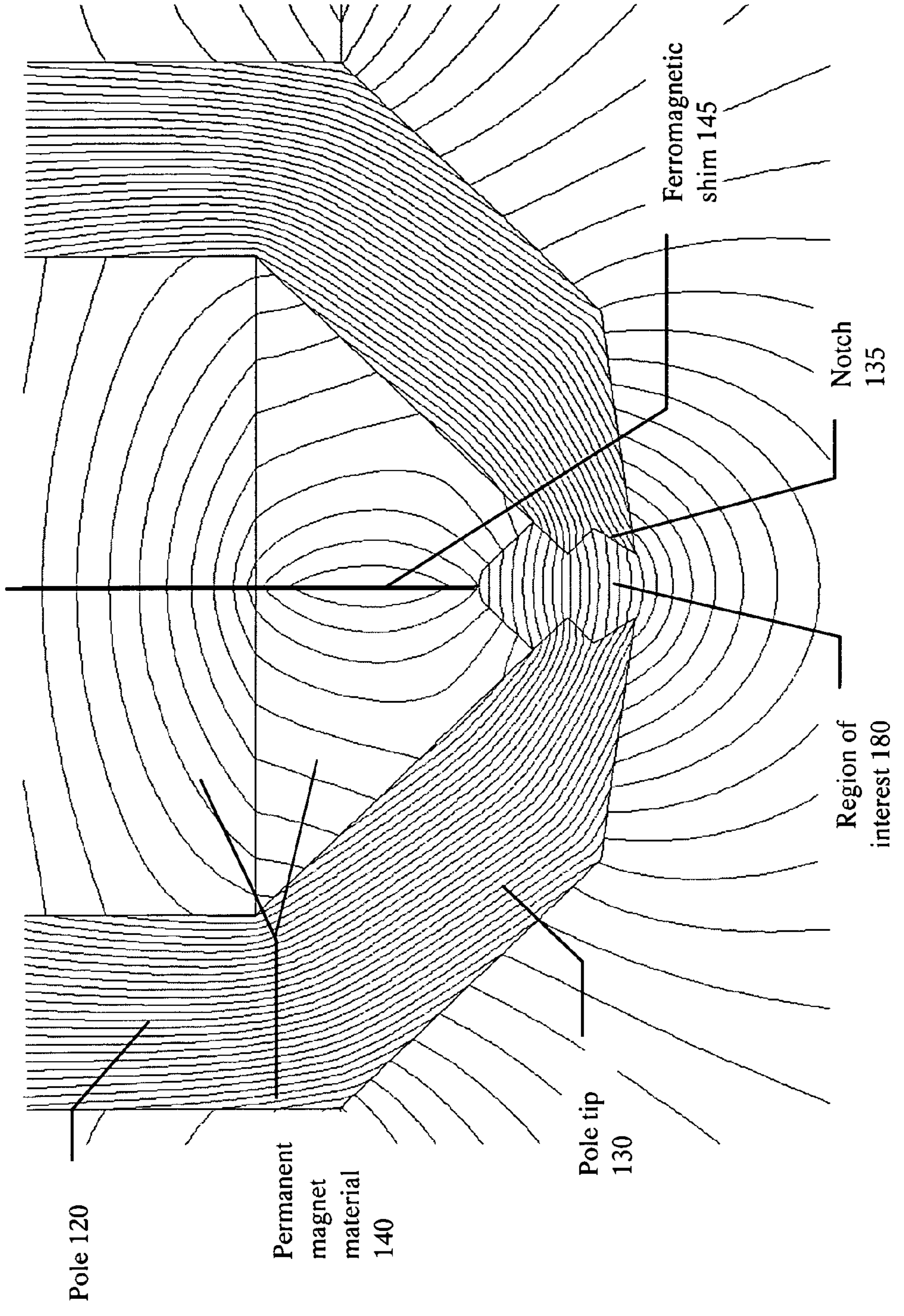
FIG. 4B shows a close-up view of the field lines through the angled pole tips and the region of interest.
Figure 4C:
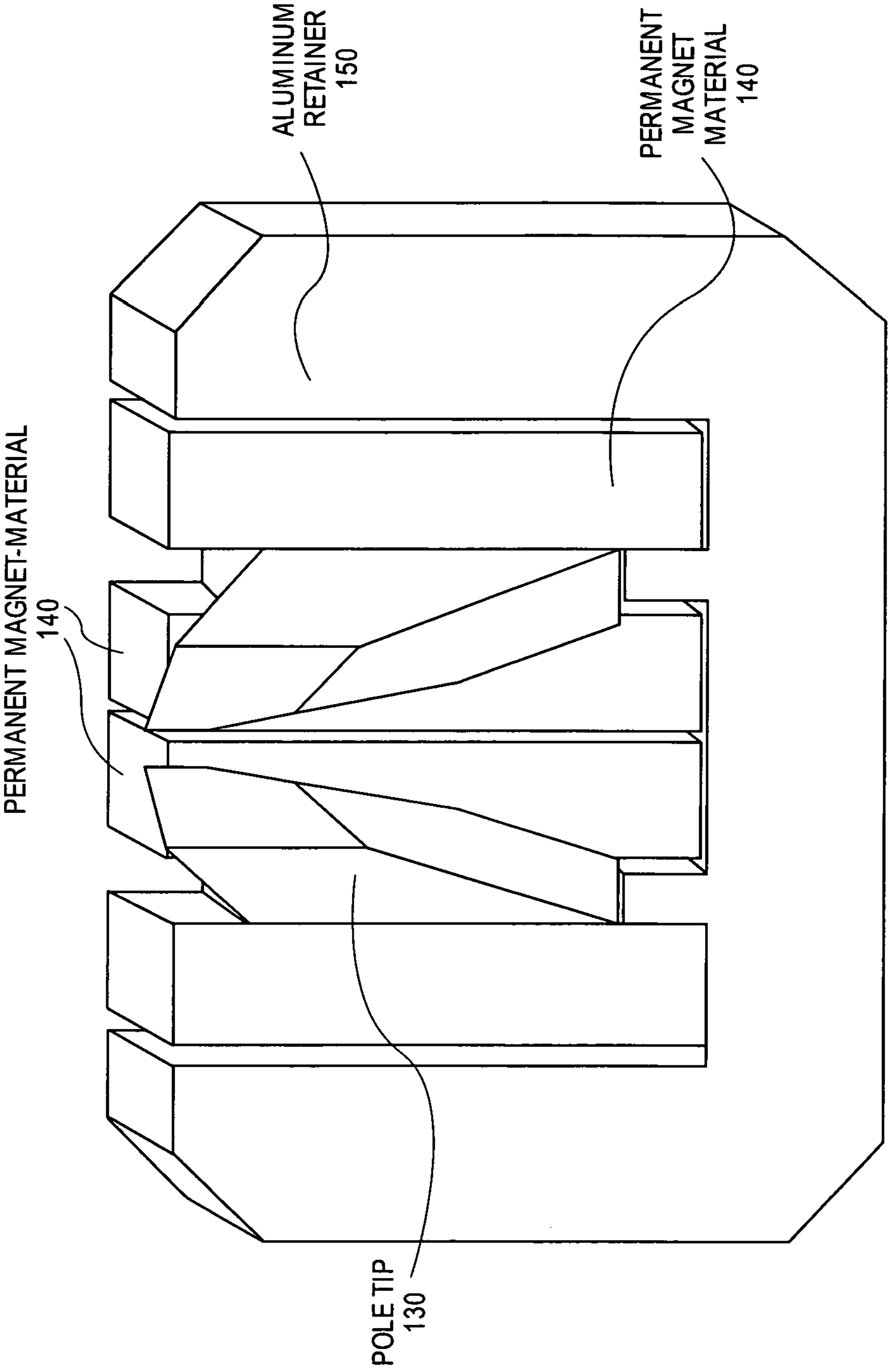
FIG. 4C shows dual parallel pole hybrid magnetic structure shown without rotating clevis frame.
Figure 5A:
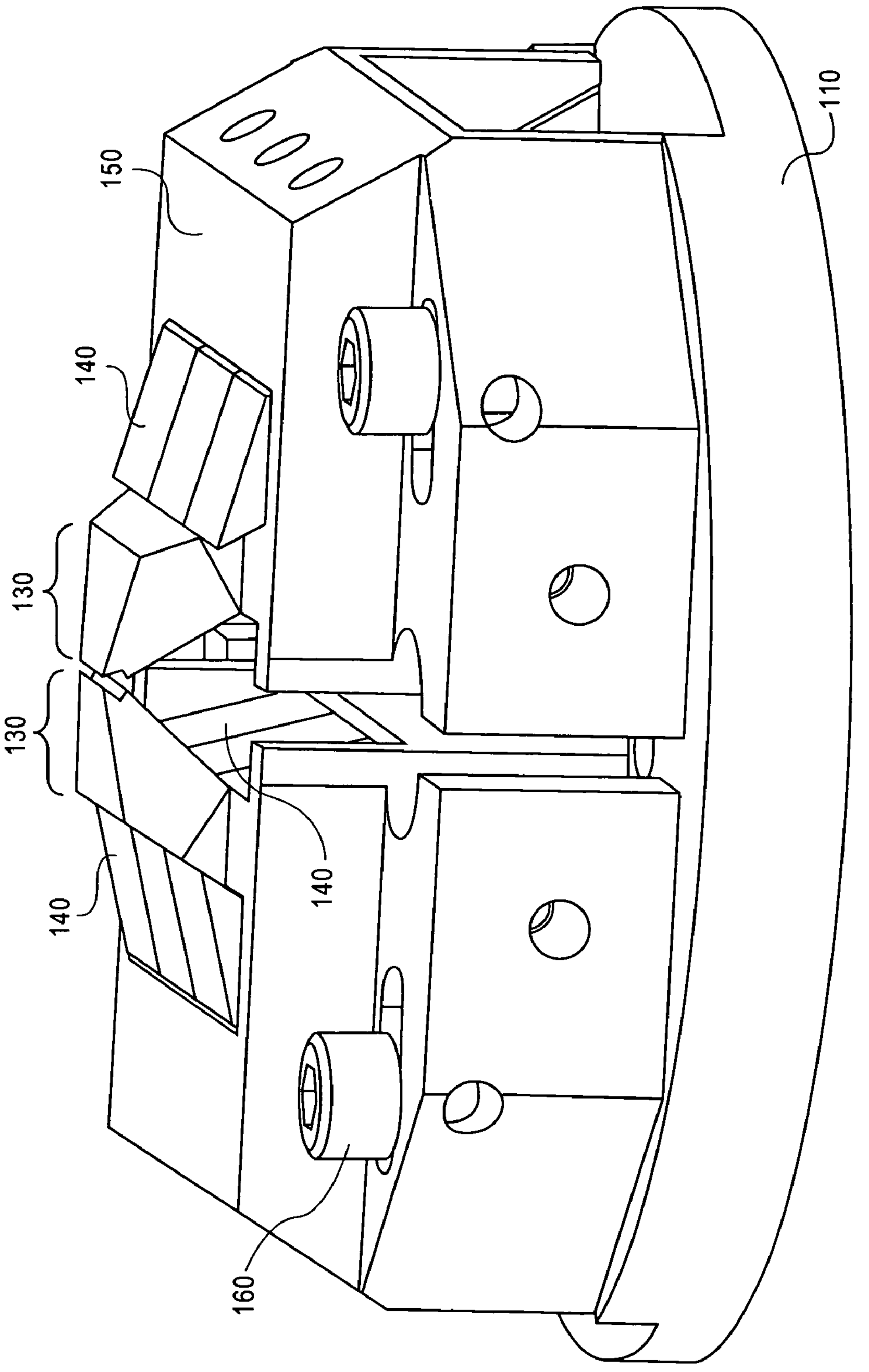
FIG. 5A is an upper view of a solid model of the assembled hybrid magnetic tweezers.
Figure 5B:
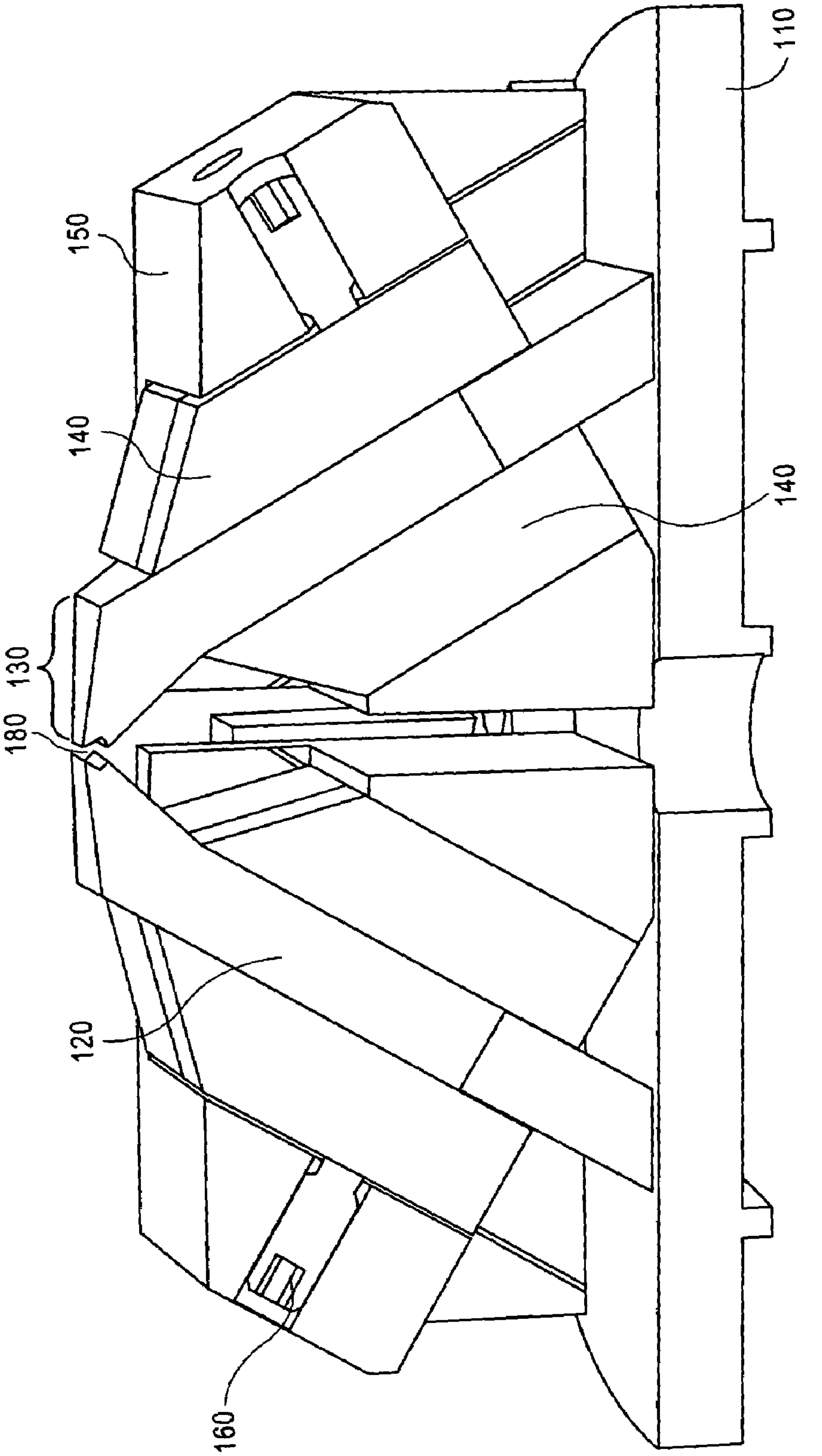
FIG. 5B is a side cross-sectional view of a solid model of the hybrid magnetic structures.
Figure 5C:
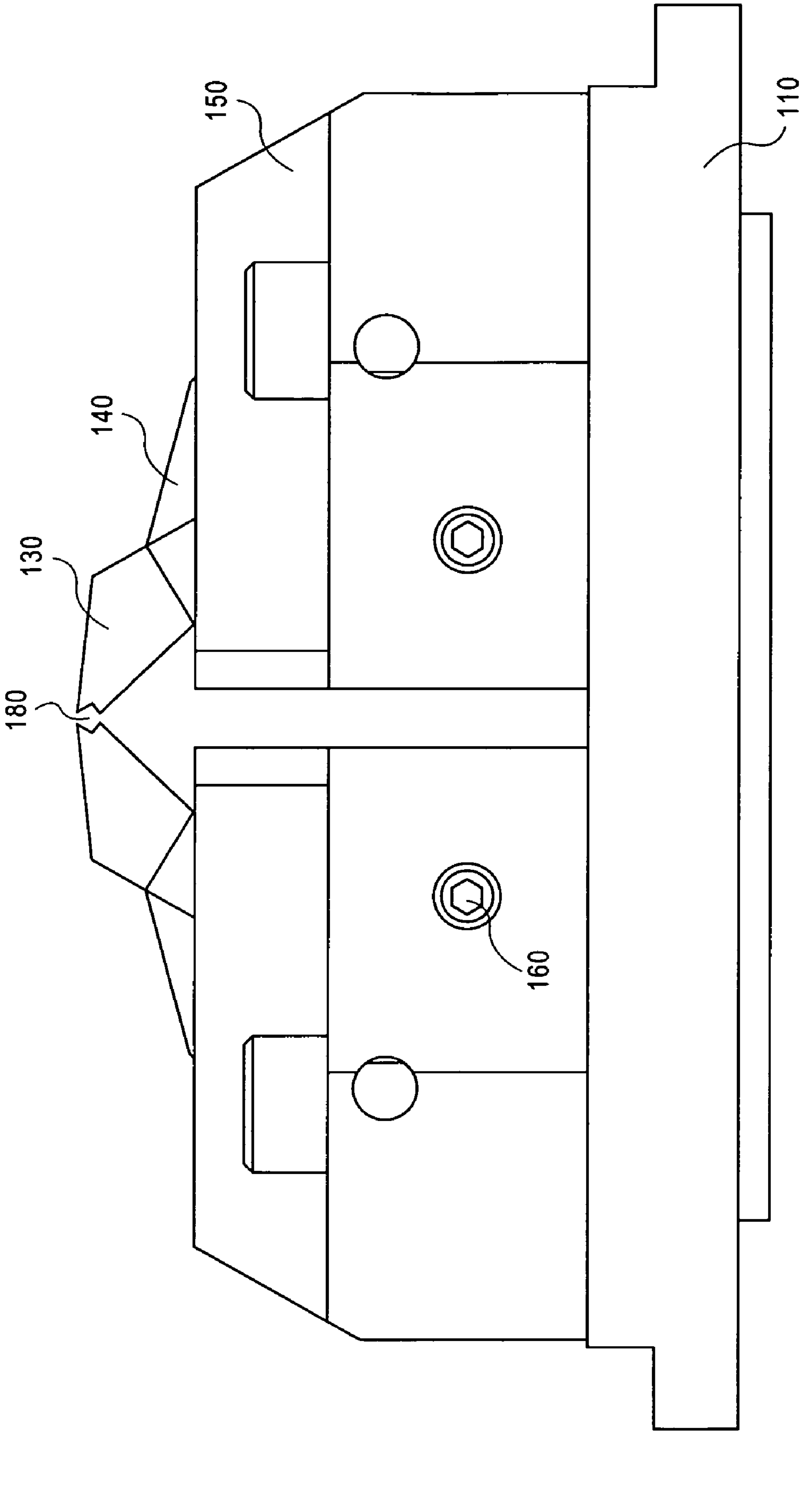
FIG. 5C is a side view of a solid model of the assembled hybrid magnetic tweezers showing the retainers and the poles sticking out above the assembly.
Figure 5D:
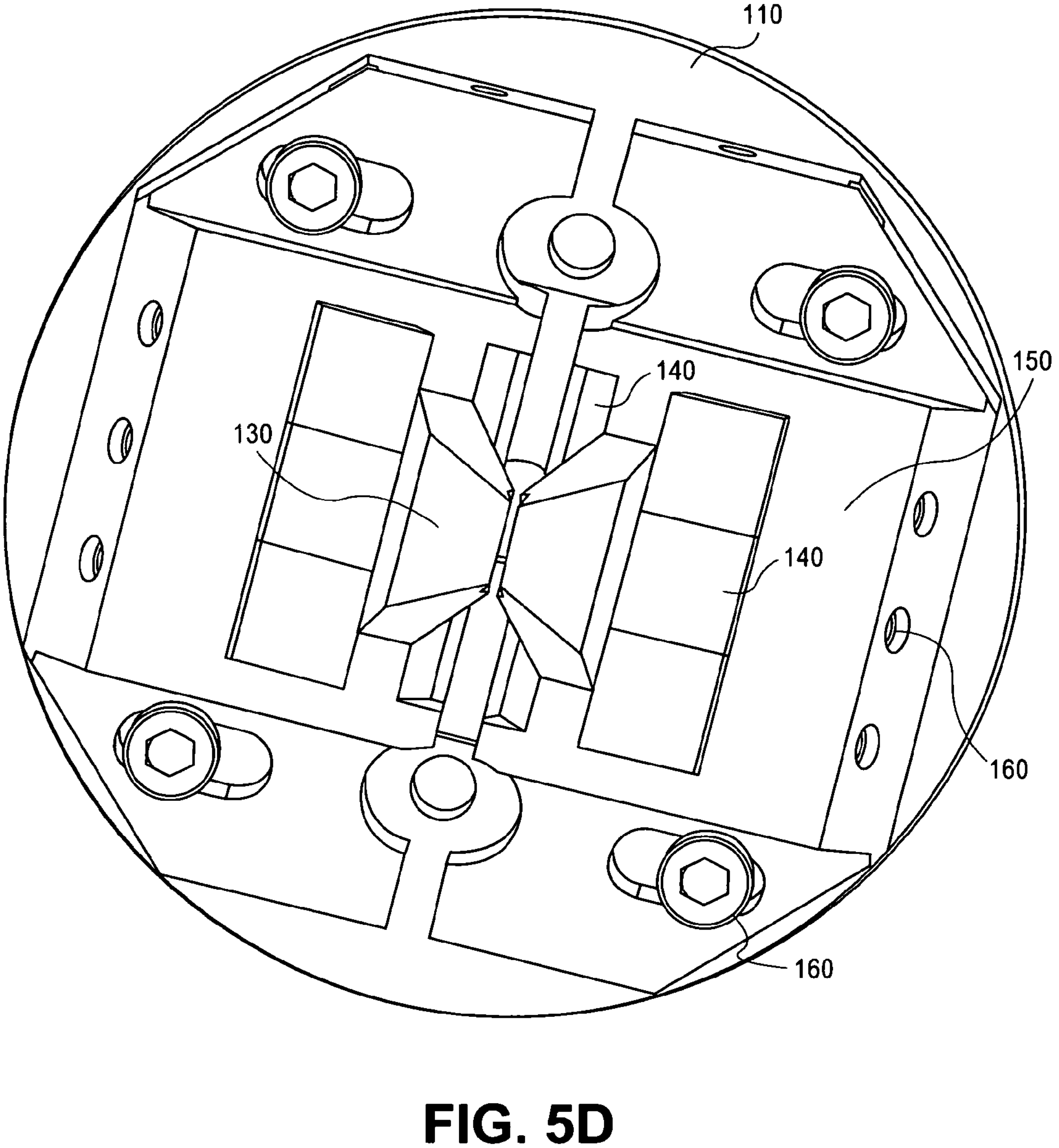
FIG. 5D is a top view of a solid model of the assembled hybrid magnetic tweezers.

Referring now to FIG. 4, the field lines shown are lines of constant vector potential of A, where A is the vector potential of Maxwell's equations. The magnetic flux density, B, can be solved from Maxwell, B=CurlA, where CurlA is given by:

$$CurlA = \nabla \times A = \left(\frac{\partial A_z}{\partial y} - \frac{\partial A_y}{\partial z}\right)\hat{x} + \left(\frac{\partial A_x}{\partial z} - \frac{\partial A_z}{\partial x}\right)\hat{y} + \left(\frac{\partial A_x}{\partial x} - \frac{\partial A_y}{\partial y}\right)\hat{z}$$

i.e., the cross product of the partial derivatives with respect to vectors x, y and z and the 3-dimensional space vector quantity A.

The curl of A is a function which acts on the vector field A. The B field is related to the rate of change in the vector potential field A. Taken together the partial derivatives of the orthogonal components of the vector potential A yield the three components of the vector field B as given in the above expression.

An implication of this relationship between the vector potential A and the magnetic flux density B is that the proximity or density of the field lines is an indication of the relative strength of the field. Therefore, as the density of field lines in close proximity increases, the stronger the magnetic field is indicated.

The fields in the ferromagnetic poles can range from several thousand gauss at the bottom to approximately seventeen thousand Gauss in the corners of the tip of a preferred embodiment. An increasing density of field lines can be seen moving from the bottom of the ferromagnetic poles to the pole tip area. The fields in the region of interest 180 outside the pole tip 130 are correspondingly high in the region of interest for magnetic applications. In addition, because of the geometry and polarity of the pole tip array, high field gradients are produced in the region of interest, which is central to the high performance of these magnetic structures. Thus, the force exerted on ferrimagnetic beads attached to target molecules in a typical process is directly proportional to the product of the B field magnitude and the gradient of the B field. Table 1 shows the simulation results of magnetic field and field gradient vs. magnet distance.

In addition, the hybrid magnetic structure increases the force maximum by at least a factor of 6 to 7 compared to magnetic tweezers without such hybrid magnets. Forces of up to ~140 pN with 2.8 μm magnetic beads and up to ~900 pN with 4.5 μm magnetic beads can be measured, which will make hybrid magnetic tweezers more than competitive with other manipulation tools even in high force range.

(3) Field Gradient Distributions

Magnetic tweezers currently in use utilize electromagnets and produce weaker fields and gradients which give poor results and require elaborate cooling systems for higher force. The instant invention differs from the currently available magnetic separators by its use of hybrid magnets which produce significantly higher fields and gradients.

The field gradient distribution in the hybrid magnetic structure is created by the combination of permanent magnets and ferromagnetic steel poles. The gradient distributions of these hybrid structures can be controlled and shaped to produce both three-dimensional, finely structured gradients with corresponding directional forces.

When designing the hybrid magnetic structure and the hybrid magnetic tweezers, the shape, size and number of soft ferromagnetic poles and the number of blocks of permanent magnet material should be directly correlated not only to the number, shape and size of the target, or the microwells or liquid containment vessels containing magnetized material that need to be acted on, but also to the desired magnetic field levels and field gradient distributions that should be created by the hybrid magnetic structure. A main objective of any adopted dimensions is to design a particular geometry of the soft ferromagnetic poles and the blocks of permanent magnet material so that an effective amount of diffuse flux from the permanent magnet material is concentrated into the ferromagnetic poles. The desired field level and gradient in the hybrid magnetic structure is strongly correlated and directly related to the quantity and the height of the permanent magnet materials, therefore increasing the height of the ferromagnetic poles and the permanent magnet material changes the shape and strength of the field gradient. See FIGS. 2, 3 and 4 for a two dimensional view of the magnetic field created by a preferred embodiment of the hybrid magnetic structure that will act on magnetized particles in a flow vessel.

The gradient of the magnetic flux density B, where B is a vector quantity in three-dimensional space and from Maxwell, B=CurlA can be solved. For a vector function such as the magnetic flux density B, the gradient of B is itself a vector which points in the direction of fastest change in B. The gradient of the magnetic flux density B is given by:

$$GradB = \nabla B = \frac{\partial B}{\partial x}\hat{x} + \frac{\partial B}{\partial y}\hat{y} + \frac{\partial B}{\partial z}\hat{z}$$

i.e., the sum of the products of the partial derivatives of B with respect to x, y and z and the unit vectors $\hat{x}$, $\hat{y}$ and $\hat{z}$. The magnitude of the gradient of B is given by:

$$|\nabla B| = \left[\left(\left(\frac{\partial B}{\partial x}\right)^2 + \left(\frac{\partial B}{\partial y}\right)^2 + \left(\frac{\partial B}{\partial z}\right)^2\right)\right]^{1/2}$$

i.e., the square root of the sum of the partial derivatives of B with respect to x, y and z.

The force $F_\nabla$ experienced by magnetized targets in the field, is proportional to the product, called the "force-density", of the field magnitude and the magnitude of the gradient of the field at the location of the target, i.e., $$F_\nabla \propto |B||\nabla B|.$$

To measure the width of a ferromagnetic spacer or shim in an embodiment such as the one shown in FIG. 4, or the amount of acceptable gap adjustment, calculation of the integral loop measures the change in the H field as it passes through the gap adjustment using the following equation:

$$\oint H \cdot dl = \mu_0 I$$

where dl is the increment of the integration path, H is the H field, and l is the integration path length increment.

C. Hybrid Magnetic Tweezers for Target Manipulation

Figure 7A:
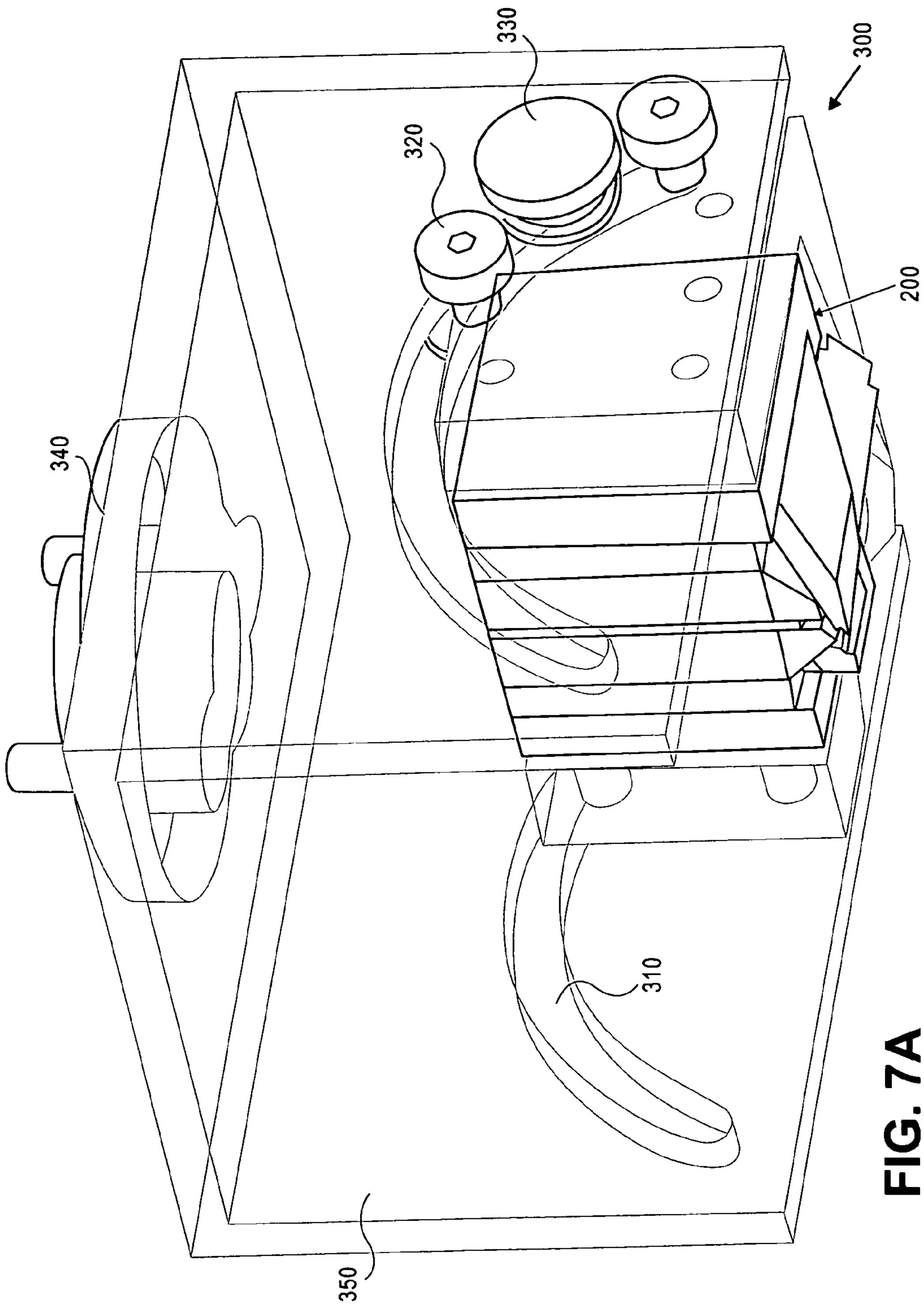
FIG. 7A shows a dual mode, parallel pole hybrid magnetic structure in horizontal mode shown in rotating clevis 300.
Figure 7B:
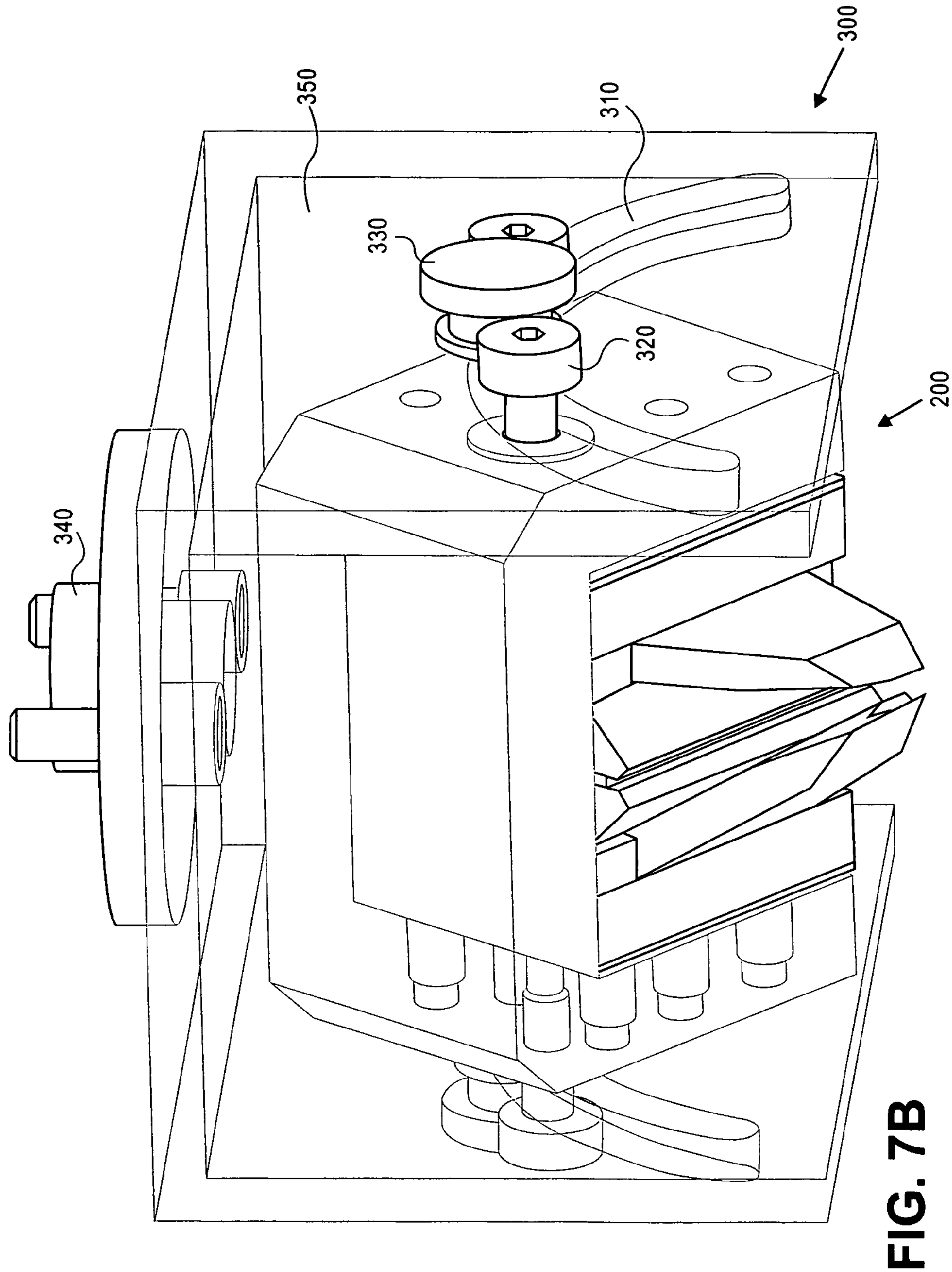
FIG. 7B shows a dual mode, parallel pole hybrid magnetic structure at 45 degree orientation in the rotating clevis.
Figure 7C:
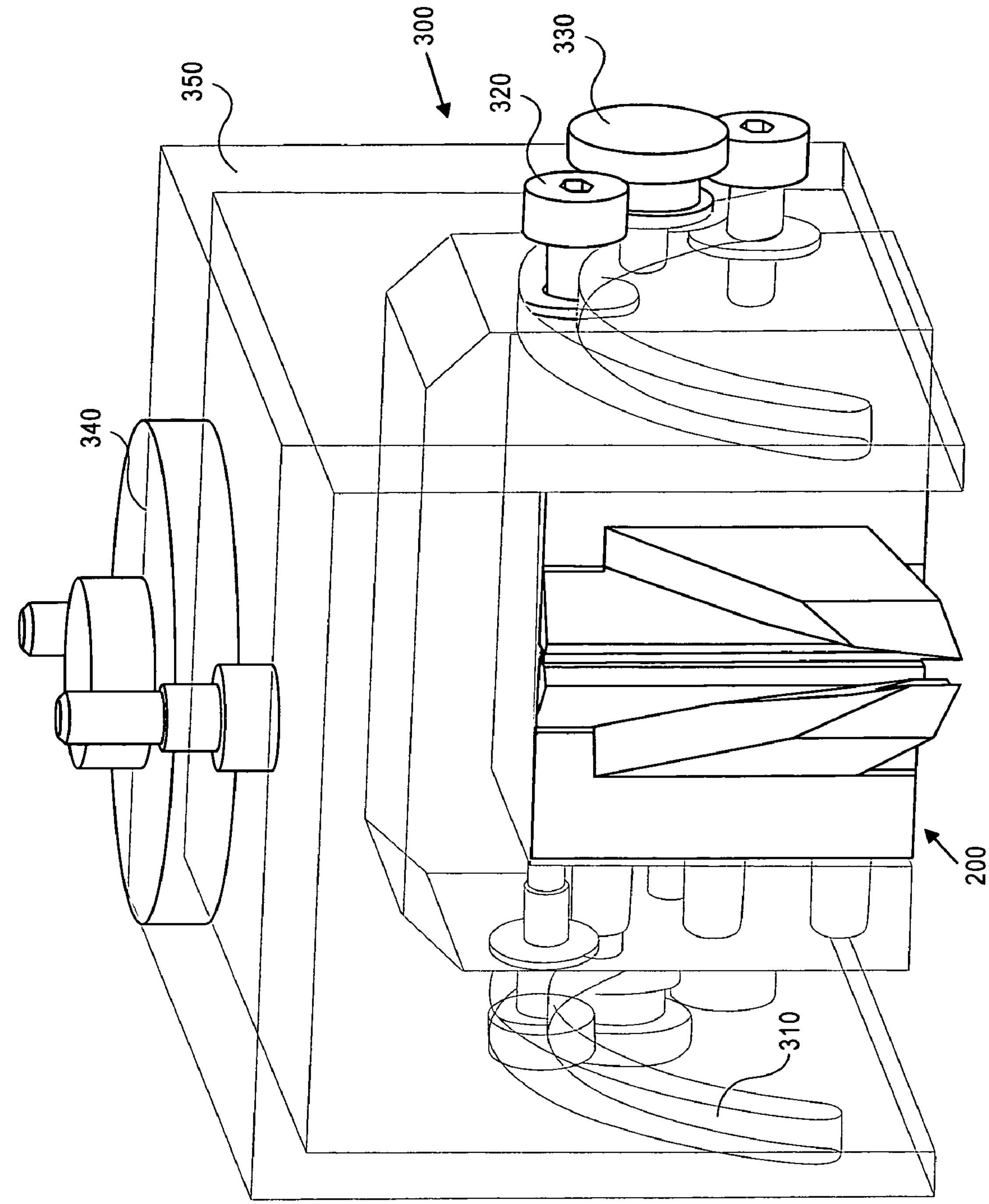
FIG. 7C shows a model of dual mode, parallel pole hybrid magnetic structure in vertical mode in the rotating clevis.

In a preferred embodiment, the hybrid magnetic tweezers are housed in a clevis 300 for precise orientation of the hybrid magnetic tweezers in relation to the target acted one. Referring now to FIGS. 7A-7C, in a preferred embodiment a clevis houses the hybrid magnetic tweezers 200 to facilitate rotation, translation and movement of the hybrid magnetic tweezers over a target area. In a preferred embodiment, the clevis is a multi-walled housing 350, having grooves or slots 310 to attach to the hybrid magnetic tweezers therein. Referring to FIG. 7, in one embodiment, the clevis holding the hybrid magnetic structure has a slot 310, wherein the structure can be moved to different Z positions or angles to increase the ranges of force applied to the target molecules using various means for fastening 320 the hybrid magnetic tweezers 200 to the clevis 300 and/or means for orientation and position control 330 within the slot 310.

In a preferred embodiment, the clevis should also have a means 340 for attaching to a rotating spindle for bi-directional rotation of the entire clevis. The rotation, speed and elevation of the clevis having hybrid magnet structure attached therein may be controlled manually or by a software program.

In one embodiment, rotation, speed and elevation of the clevis containing the hybrid magnetic tweezers should be controlled by motor control of translation and rotation. The motor control should be at least capable of turning the clevis at intervals of 1 Hz and move <1 mm/sec.

In a preferred embodiment, the hybrid magnetic tweezers 200 are housed in a clevis 300 and used in an apparatus 400 comprising a light source, optics with a set of lenses, hybrid magnet tweezers comprising at least one hybrid magnetic structure 200 mounted in a clevis 300, a flow vessel 210 having a target 205, the target comprising a molecule or particle having a magnetic bead attached, an objective lens and a CCD camera. (FIGS. 8A-8D). Target molecules and particles attached to the substrate can be mechanically manipulated by applying force and torque via a magnetized particle attached to them as described in the next section. Furthermore, the effects of dipole or monopole hybrid magnetic structures in the hybrid magnetic tweezers can be designed with the end function in mind according to the teachings of the present application.

In one embodiment, the apparatus comprises a light source, collimating optics with a set of lenses, the hybrid magnet structure 200 mounted in a clevis 300, a flow cell containing the target attached to the flow cell, the target comprising a molecule or particle having a magnetic bead attached, an objective lens and a CCD camera. Target molecules and particles inside the flow cell can be mechanically manipulated by applying force and torque via the magnetic bead attached to them. In such an embodiment, the hybrid magnetic structure should be capable of rotation to induce torque force on the magnetic beads attached to the targets. The force by the hybrid magnetic structure may vary depending on Z position of the ferromagnetic poles and pole tips.

Figures 8A, 8B:
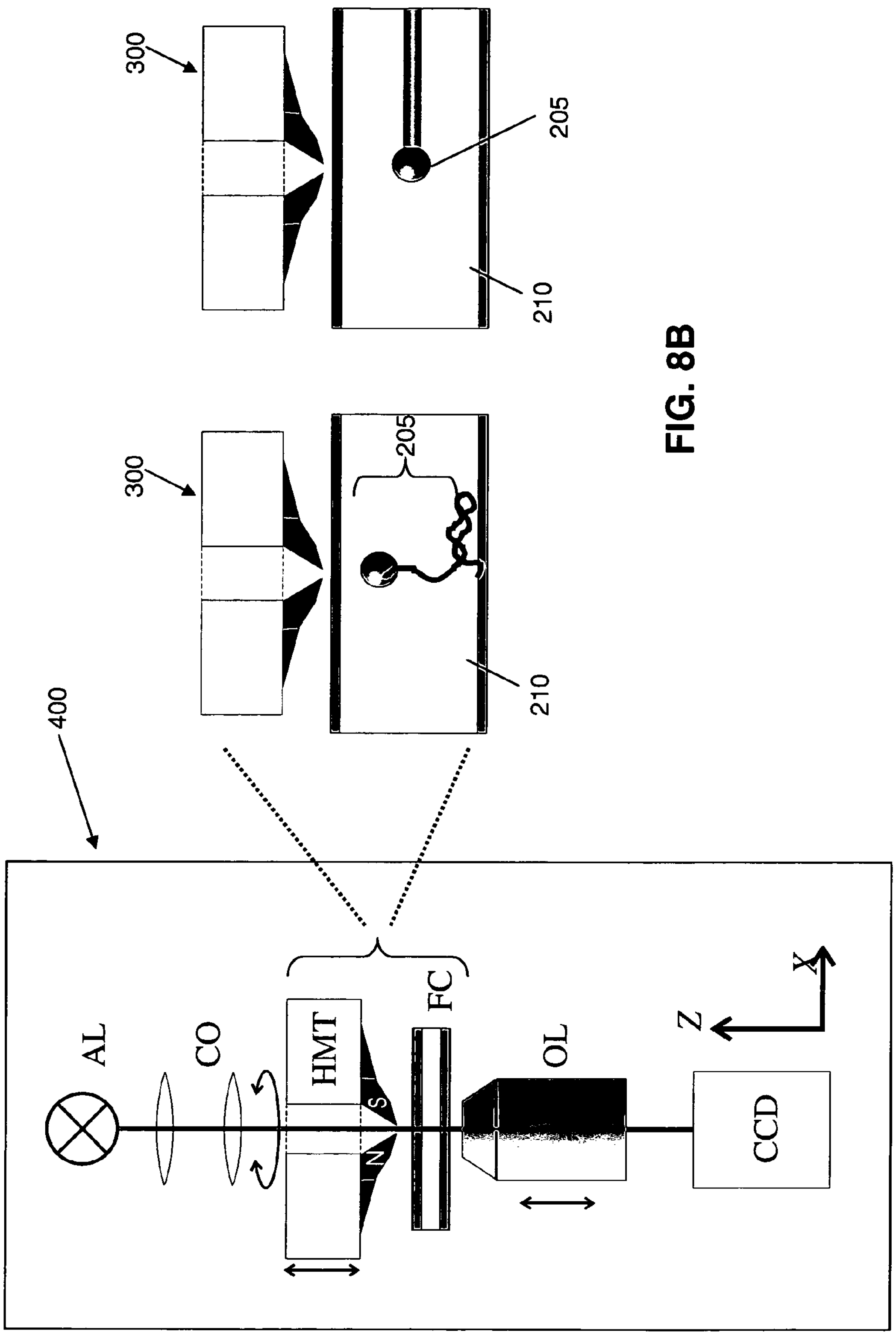
FIG. 8A shows a schematic of the hybrid magnetic tweezers used in the apparatus 400.
FIG. 8B shows magnified views of the hybrid magnetic tweezers with a flow cell having a target attached to a magnetic bead. Two experimental configurations: (left) A DNA molecule attached on the glass surface is pulled upward by magnetic force on the magnetic bead. Here, supercoiled DNA molecule is shown; (right) a flexible glass pipette is pulled upward by the same magnetic force. Typical images in the two experimental configurations are shown in the inset in FIG. 11A.
Figure 10:
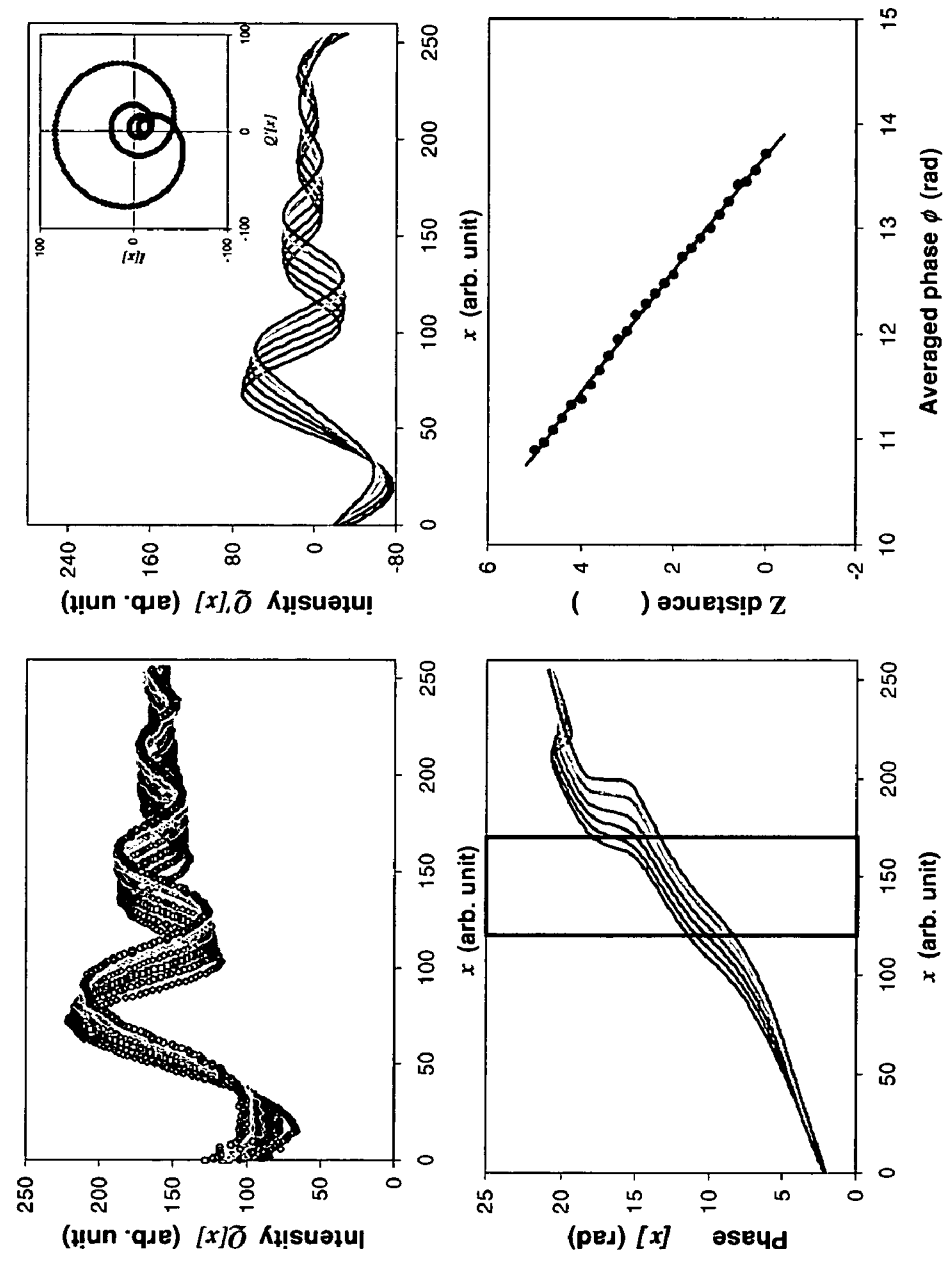
FIG. 10 are graphs showing the results of Hilbert transformation scheme. (A) Radial intensity profiles Q[x] by a bead vs. the distance from the center (x). Six profiles are shown here for 6 different Z values in 1 μm interval (in the order of black, yellow, orange, green, red, and blue). The color convention holds in (A), (B), and (C).

Referring to the schematics shown in FIG. 8A, the force by the hybrid magnetic structure varies depending on the Z position of the ferromagnetic poles and pole tip. Torque on magnetic beads is induced by rotating the hybrid magnetic tweezers (HMT). In one embodiment, magnetic beads in a flow cell (FC) are imaged on a CCD camera by an objective lens (OL). AL is an arc lamp and CO is collimating optics with a set of lenses. The red line depicts illumination. FIG. 10A and Table 1 show a simulation result of magnetic field and field gradient along the z axis.

In another embodiment, a microscope stage wherein XY translations by manual motor stages and Z is fixed. An objective lens should be mounted in a system for motor controlled fine movement and manual Z mount for coarse adjustment.

In another embodiment, the source lamp should illuminate a sample after passing a red filter, lenses and a pinhole. In a preferred embodiment, light passing the sample is sent to CCD detectors through an objective, a mirror and a focusing lens.

In another embodiment, the software for control and data acquisition can be a commercially or academically available framegrabber program and plotting program. In another embodiment, programs that control the motors and other control systems.

D. Applications of Hybrid Magnetic Tweezers

Herein we demonstrate that hybrid magnetic tweezers are a very powerful tool for studying single molecule biophysics by overcoming force limitations and improving analysis schemes. The dynamic range of the force that can be applied by the new magnetic tweezers to a magnetic bead attached to a target molecule is from a few fN to about 1 nN.

In one embodiment, by ensuing improvement in material and design, it is contemplated that the forces applied by the hybrid magnetic tweezers will go beyond 1 nN without altering the size or type of beads (for example, larger diameter beads). This range of force will cover forces involved in interesting biological phenomena, for example the bonds of tightly bound target molecules, for example, the breakage of DNA molecules by force during chromosome segregation. For example, using an asymmetric dipole hybrid magnetic structure in the hybrid magnetic tweezers, within the region of interest, field strengths have been measured at about 0.8 T. Within the gap between pole tips, field strengths have been measured at 1.5 T. In another example, using a parallel dipole hybrid magnetic structure in the hybrid magnetic tweezers, where the region of interest is between the poles in one mode, field strengths have been measured at about 0.75 T.

In addition to the extended force range, the selectivity of the hybrid magnetic tweezers to magnetically labeled molecules may allow the manipulation, capture or separation of such complicated extra-cellular and intra-cellular phenomena in vivo because the hybrid magnetic tweezers will not interfere with other intra-cellular organelles. One can exert high force to macromolecules with AFM (Rief, Gautel et al. 1997; Carrion-Vazquez, Oberhauser et al. 1999), but it cannot apply force below tens of pN and relies on direct contact with the target molecule. Thus it is contemplated that the hybrid magnetic tweezers can be used for flow separation, capture and manipulation of target molecules in vivo. It is contemplated that magnetically labeled target molecules may be captured or manipulated by the hybrid magnetic structures of the present invention in a blood vessel or body cavity in vivo.

In a preferred embodiment, these field distributions described above are able to create both a force vector and an orienting vector that can act on a magnetized particle attached to a target molecule. In one embodiment, the magnetized particle is a magnetic bead attached to the end of a single strand of DNA or similar long-chain molecule, while the other end of the strand is attached to a substrate or capillary tube wall. The force and orientation vectors, acting on such a magnetic bead, allow the molecular strand to be manipulated by stretching and/or twisting actions. The manipulation of the molecular strand may be performed in proximity to a microscopy instrument in order to observe the behavior of the molecule. Any magnetic beads or particles that are, or typically contain, ferrimagnetic material can be used in conjunction with the hybrid magnetic tweezers. Appropriate magnetic beads may range in diameter from 50 nm (colloidal "ferrofluids") to several microns. Many companies have developed biological (e.g. antibody-, carboxylate-, or streptavidin-coated) and chemically activated (e.g. Tosyl group or amino group) magnetic particles that would prove useful in magnetizing molecular structures and targets and thus then be acted upon by the hybrid magnetic structure.

In one embodiment, the hybrid magnetic tweezers can be used to apply forces on target molecules covalently or non-covalently attached to a substrate or surface. In some embodiments, the attachment of target molecules such as DNA on a surface relies on rather weak antibody binding and therefore any phenomena happening to DNA at force enough to break the binding will not be observed. In a preferred embodiment, the target molecule is attached by multiple antibody binding, such that the maximum force applicable without breaking the binding will be higher. For high force requirements, stronger binding such as covalent linking may be necessary. For example, application of such a high force will be very useful in studying the movement cooperatively induced by many motor proteins such as chromosome segregation by kinesins on microtubules during mitosis and meiosis. In addition to the extended force range, the selectivity of hybrid magnetic tweezers to magnetically labeled molecules may permit the study of complicated intra-cellular phenomena.

In addition to force capability, the hybrid magnetic tweezers can apply torque very conveniently—by simply rotating the hybrid magnet tweezers over the target molecule, making the hybrid magnetic tweezers a versatile tool to study DNA supercoils and topoisomerases (Strick, Allemand et al. 1996; Strick, Croquette et al. 2000). In the prior art, in order to apply torque with laser tweezers, one would build a rather sophisticated rotating pipette system such as the one that was used to study *E. Coli* Topo IV (Stone, Bryant et al. 2003). In a preferred embodiment, a means for mounting the hybrid magnetic structure is made to maintain the correct distance between the hybrid magnet tweezers and the target molecule being acted upon. In one embodiment, the means for mounting can be attached or removably attached through the base.

In a preferred embodiment, wherein a clevis houses a hybrid magnetic structure to facilitate rotation, translation and movement of the hybrid magnetic structure over a target area, different modes of force acting upon a target molecule can be achieved. The clevis has slotted holes by which the hybrid magnetic structure can be slid into various orientations with respect to the target area. Using a parallel dipole hybrid magnetic structure in the hybrid magnetic tweezers, a molecule can be oriented horizontally (i.e., laid on its side or stretched horizontally) when the pole tips straddle the capillary tube or flow cell (FIGS. 7A-7B). In another mode, using the parallel dipole hybrid magnetic structure, the structure is rotated 90 degrees so the pole tips are in a vertical position (FIG. 7C) to exert upward, twisting or rotating forces, such as unwinding and stretching.

Figure 12A:
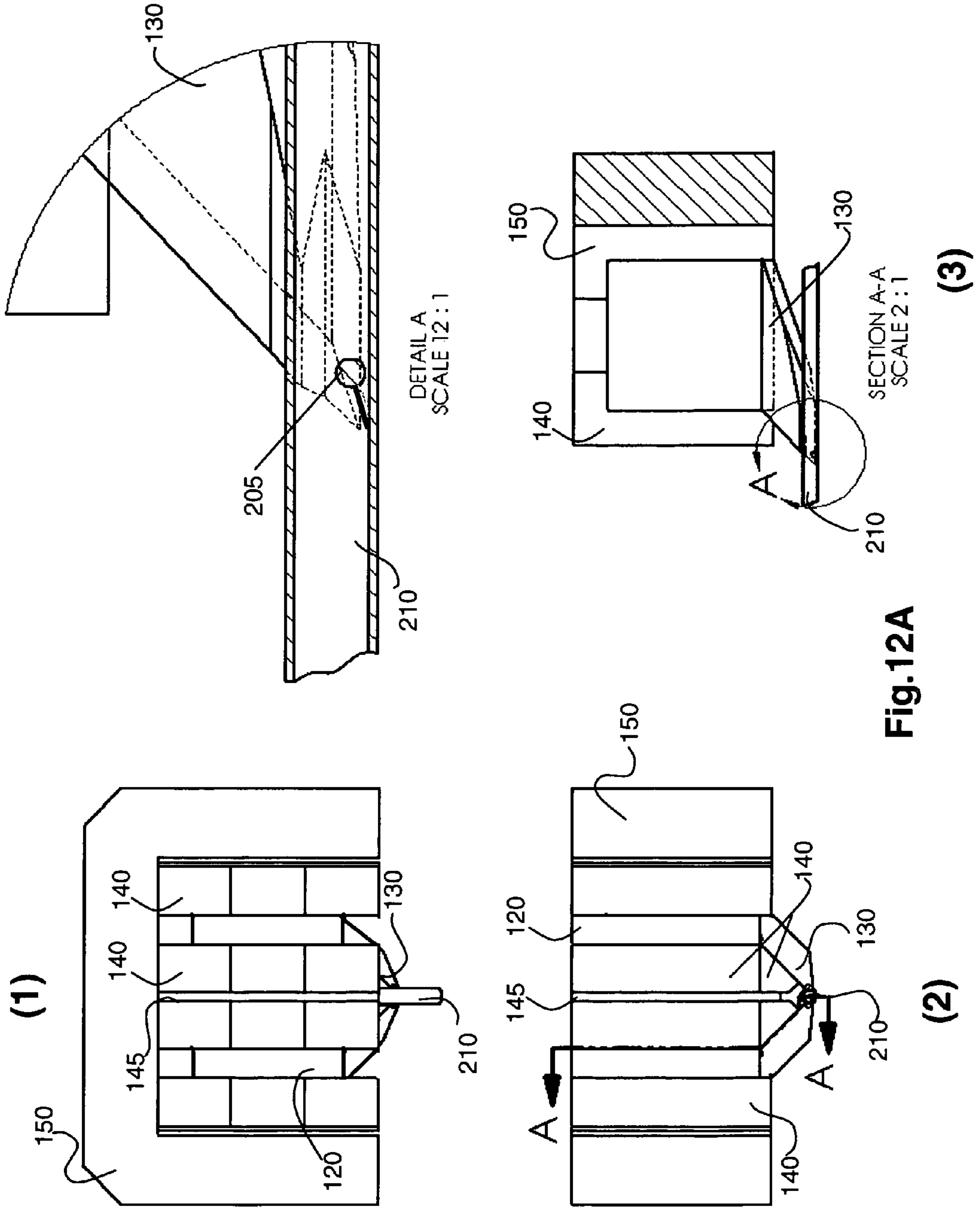
FIG. 12A shows a top (1), front (2) and side (3) view of a dual mode magnetic structure with pole tips straddling a flow cell containing a magnetized strand of DNA. Detail "A" of this figure shows the DNA strand being pulled towards a horizontal orientation.
Figure 12B:
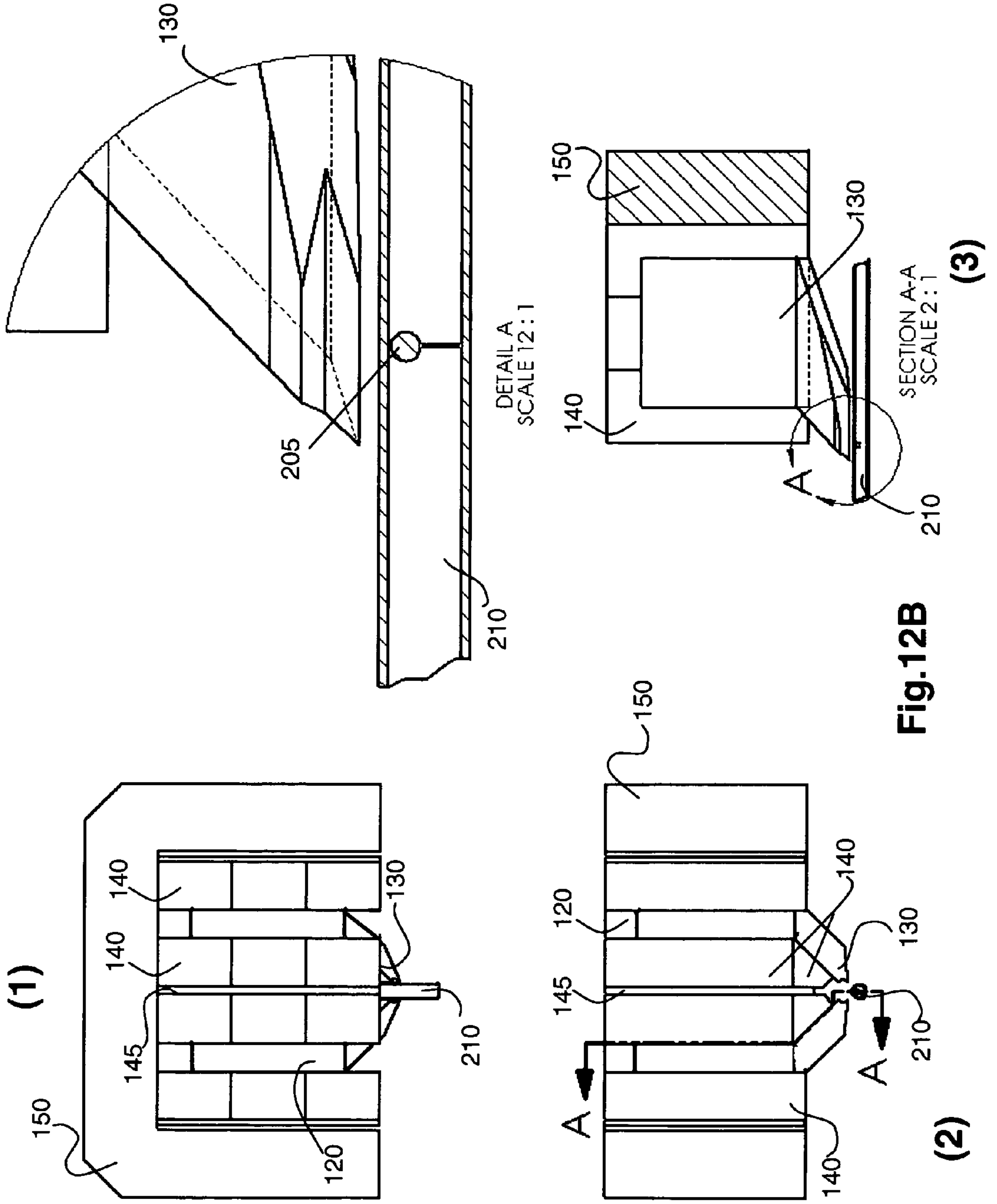
FIG. 12B shows a dual mode magnetic structure with the same orientation as that of the structure of FIG. 12A, that has been elevated above a flow cell containing a magnetized strand of DNA. Detail "A" of this figure shows the DNA strand being pulled in the vertical direction.

In a preferred embodiment shown in FIG. 12A, using a parallel dipole hybrid magnetic structure 200 without a clevis, a molecule can be oriented horizontally (i.e., laid on its side or stretched horizontally) when the pole tips 130 straddle the capillary tube or flow cell 210. Detail A shows the relationship of the pole tips 130, the flow cell 210 and the magnetized molecule 205. In another mode, shown in FIG. 12B, using the same parallel dipole hybrid magnetic structure, the magnetic structure is elevated and translated without changing its angular orientation so that the pole tips 130 and their peak field location are positioned above the magnetized molecule 205 to vertically orient the molecule and exert an upward force. In this mode the magnetic structure 200 can be rotated about a vertical axis to exert twisting or rotating forces, for winding or unwinding the molecule. Stretching forces can be controlled by varying the proximity of the pole tips 130 above the magnetized molecule 205. After unwinding a molecule, the magnetic structure can be translated and lowered so that the pole tips are again straddling the flow cell and the unwound molecule is now oriented horizontally for investigating via microscopy techniques.

As one desires to combine force manipulation method with visualization tool such as fluorescence microscopy, magnetic tweezers are ideal because they dispense with laser usage that may bleach dye molecules or interfere with lasers used in single molecule fluorescence microscopy.

Figure 13A:
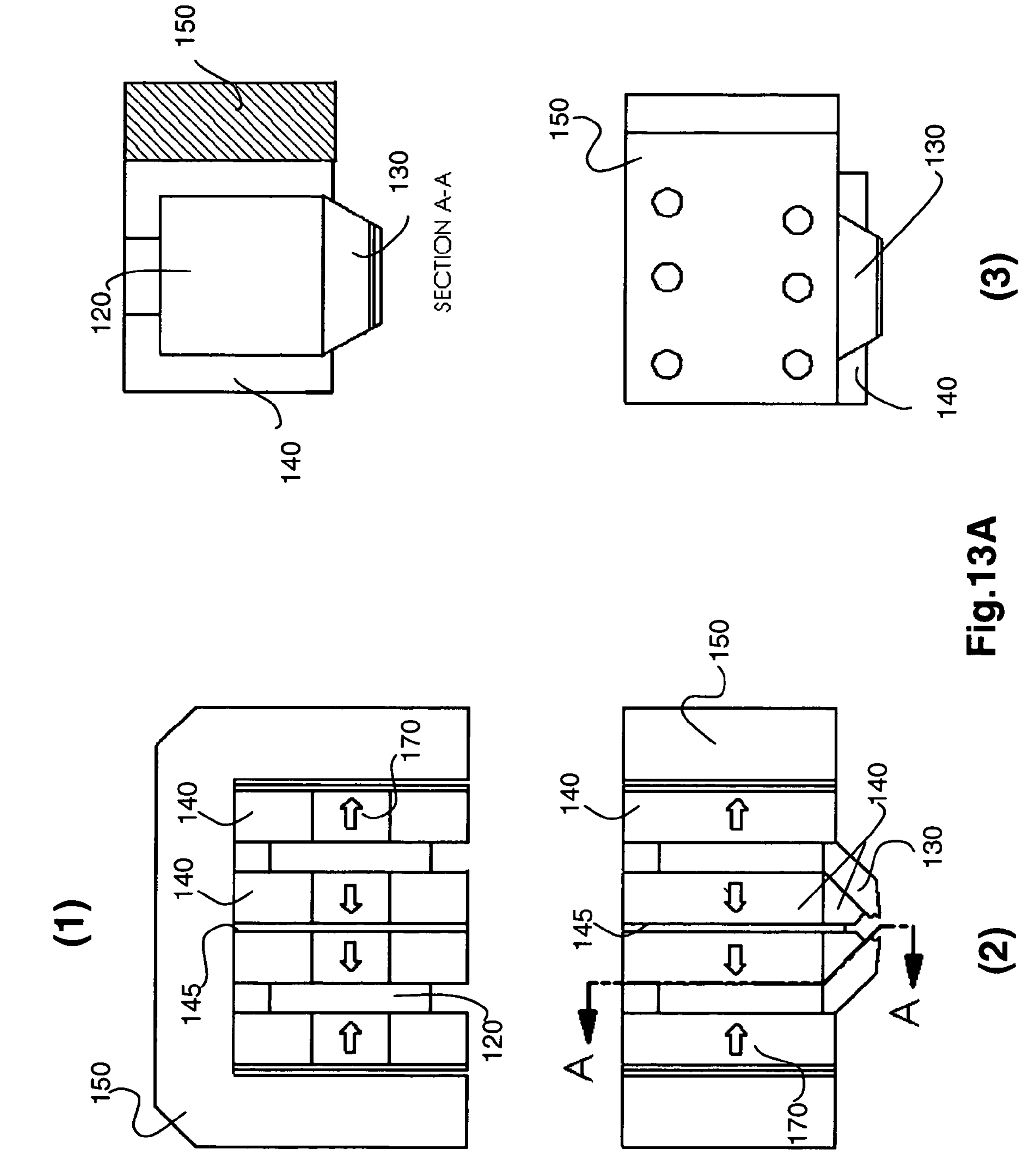
FIG. 13A shows top (1), front (2) and side (3) view and a section view of a parallel pole magnetic structure with a pole tip shape that has been designed for use with a flow vessel. Section A-A shows the pole shape with elongated tip 130.
Figure 13B:
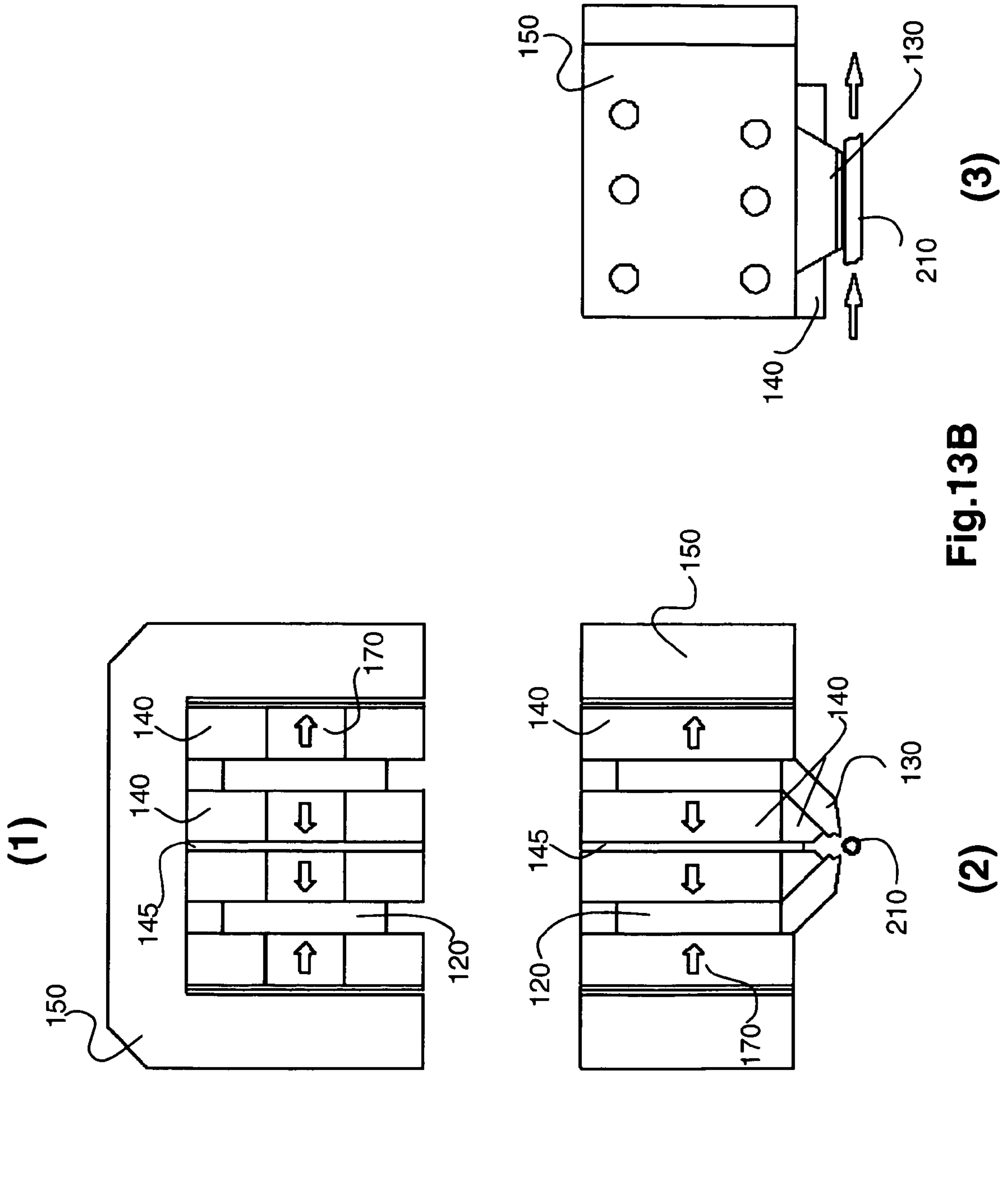
FIG. 13B shows the magnetic structure of FIG. 13A with a flow vessel in proximity to the pole tips of the magnet to allow flow separation of magnetized targets passing through the vessel.

In another application, the hybrid magnetic tweezers can be used for flow separation, capture and manipulation of target molecules. It is contemplated that magnetically labeled target molecules may be captured by the hybrid magnetic structures of the present invention in a flow cell or flow vessel. A preferred embodiment for this application is shown in FIGS. 13A and 13B. FIG. 13A shows a top (1), front (2) and side (3) view of a parallel pole magnetic structure. Section A-A of FIG. 13A shows the shape of the pole 120 which has a wide pole tip 130. FIG. 13B shows the same magnetic structure in proximity to a flow vessel 210. The wide pole tip 130 allows the strong gradient fields at the pole tip to act over a longer length of the flow vessel 210 and more effectively separate targets from the volume flowing through the vessel.

EXAMPLE 1

Fabrication of Hybrid Magnetic Structures for Hybrid Magnetic Tweezers

We fabricated special magnets for our magnetic tweezers (FIG. 2 (*a*)) to get high force field as follows. A pair of hybrid magnetic structures were placed ~0.8 mm apart with opposite polarities adjacent. These magnet devices generate a very large field and field gradient based on the hybrid magnet technology (Humphries 2001). The hybrid magnetic structure was developed initially in the Lawrence Berkeley National Laboratory and Joint Genome Institute (JGI: Department of Energy) for DNA separation (Humphries 2001). Here, we described the development of hybrid magnetic structures for the magnetic tweezers as a single macromolecule manipulation tool. Each hybrid magnetic structure was assembled by sandwiching an iron pole piece (1006 Steel) between a pair of rare-earth magnets (Nd:Fe:B) with the same polarity facing the pole piece. The magnetic field was concentrated through the pole piece in the gap between the two pole tips and quickly decayed away from the gap. This created a strong field gradient that maximized the force exerted by the magnetic tweezers. The tip was specially shaped so that the field gradient near the pole was maximized as shown in FIGS. 2A and 2B. Based on numerical simulations with the 'Poisson Superfish' program (LANL) that is designed to calculate 2D magnetic fields (FIGS. 2B and 10A-10B) from 2D magnetic structures and utilization of 3D magnetic design principles, we optimized the 3D configuration of the hybrid magnetic structures for the best performance.

EXAMPLE 2

Apparatus for Molecular Target Manipulation and Capture

FIG. 8A shows the schematic diagram of the magnetic tweezers we constructed. Some basic features were adopted from that previously reported by Strick, Allemand et al. 1996, which is hereby incorporated by reference. The hybrid magnetic tweezers were used in an apparatus comprising a light source, collimating optics with a set of lenses, the hybrid magnet structure mounted in a clevis, a flow cell containing the target, the target comprising a molecule or particle having a magnetic bead attached, an objective lens and a CCD camera. DNA molecules inside the flow cell can be mechanically manipulated by applying force and torque with a pair of magnets to the magnetic bead attached to one end of the DNA. The magnets are attached to the bottom of a cylindrical spindle that has a hole in the middle for illumination of the flow cell. Rotation and translation of the magnet assembly are driven by two computer controlled (Polytec PI motor control card C-843) stepping motors with built-in position encoders (Polytec PI, M126.DG and C-136.10).

Sample and Flow Cell Preparation

DNA molecules used in this study were prepared from pPIA2-6 plasmid (Forde, Izhaky et al. 2002) digested with the BamH I and Sal I restriction endonucleases. The 14.8 kb product was purified by agarose gel electrophoresis and ligated to DNA linkers (~500 bp) generated by digestion of PCR products modified by either biotin-16-dUMP or digoxigenin (Dig)-16-dUMP residues (Roche Molecular Biochemicals).

Flow cells were constructed by sandwiching a sheet of Nesco film between a pair of 1 oz coverslips (VWR Scientific) cleaned with acetone and purified water. An aperture cut in the middle of the Nesco film serves as the experimental chamber (approximately 20 μl) and the cell was sealed by heating. DNA molecules and beads were delivered to the chamber through holes in one of the coverslips. For the measurement of force by pipette bending, a short piece of glass tubing (ID=100 μm) that tunnels into the chamber a tapered pipette was sandwiched between the coverslips.

To fix DNA molecules in the flow cell as shown in FIG. 8B (left panel), the cell was coated with antibody to Dig (Roche: 1 mg/ml) in phosphate buffer saline (PBS) plus 10 mM sodium azide overnight and then with sonicated salmon sperm DNA (Invitrogen: 3.35 mg/ml) and acetylated bovine serum albumin (BSA) (Sigma: 10 mg/ml) for 12 hours. Biotin- and Dig-labeled DNA molecules were incubated with Streptavidin-coated magnetic beads (2.8 μm: Dynal Biotech) for 10 minutes and introduced and bound to the flow cell at the Dig-labeled end. After 20 min, unbound beads and DNA molecules were washed out of the chamber with PBS. Some of bound DNA molecules were torsionally constrained.

To prepare 4.5 Mm magnetic beads for DNA tagging, Tosyl-activated M500 Subcellular from Dynal Biotech were incubated with Streptavidin (Pierce: 20 μg in 100 μl of 0.1 M borate pH 9.5) overnight according to Dynal's procedure for binding antibody to the beads. For pipette bending experiments, the same M500 beads were blocked with a mixture of Tris-base (25 mM) and glycine (250 mM) at pH=8.3 overnight to avoid non-specific sticking of the beads to the pipette.

For measurement of force by pipette bending (see FIG. 8B (right panel)), thin-walled hollow pipettes (World Precision Instruments: OD=1 mm) were pulled by a Sutter P-97 pipette puller. The flexibility of the taper was adjusted to the desired range by varying pulling conditions. The tip of the pipette (a few μm in diameter) was trimmed square by cutting the end with a heated platinum wire to obtain a good seal with a bead.

Hybrid Magnetic Tweezers Apparatus

Figure 8C:
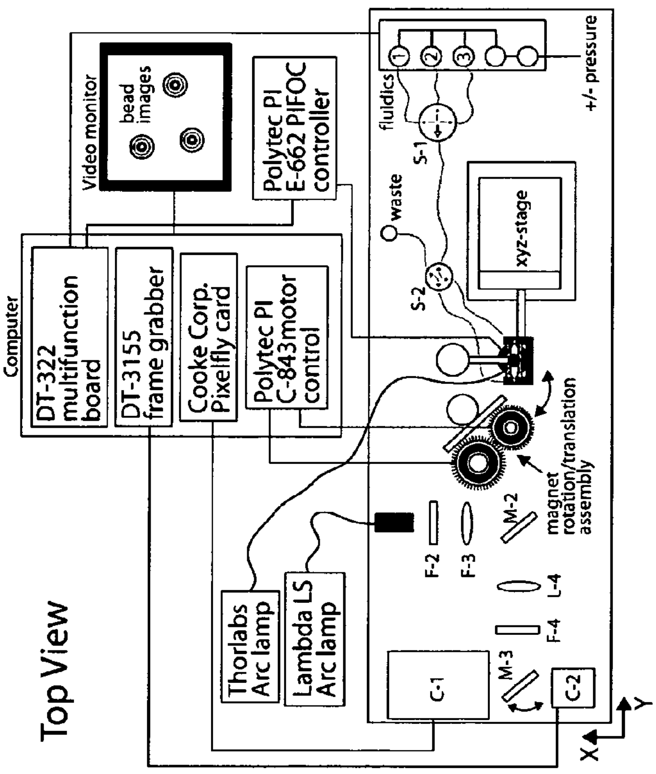
FIG. 8C shows a top view of the apparatus 400 in detail. The force exerted by the magnetic tweezers depends on the distance along Z of the hybrid supermagnets to a magnetic bead in the flow cell. Torque on the magnetic bead is induced by rotating the magnets. Beads in the flow cell are imaged on the CCD cameras (C-1 and C-2) by an objective lens. L-1, L-2, and L-3 are collimating lenses and L-4 is a focusing lens. F-1, F-2, F-3, and F-4 are a red filter, a neutral density filter, an excitation filter, and an emission filter, respectively. M1, M2, and M3 are a 45° mirror, a dichroic mirror, and a flip mirror, respectively. S-1 and S-2 are switches for the micro-fluidics system.
Figure 8D:
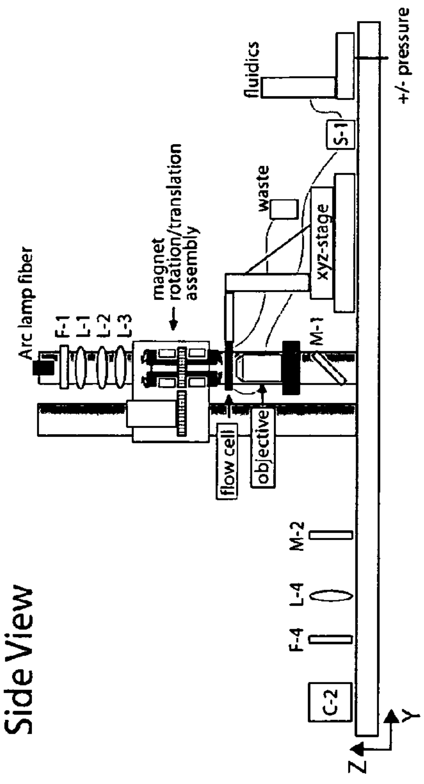
FIG. 8D shows a side view of the apparatus 400 in detail.
Figure 9A:
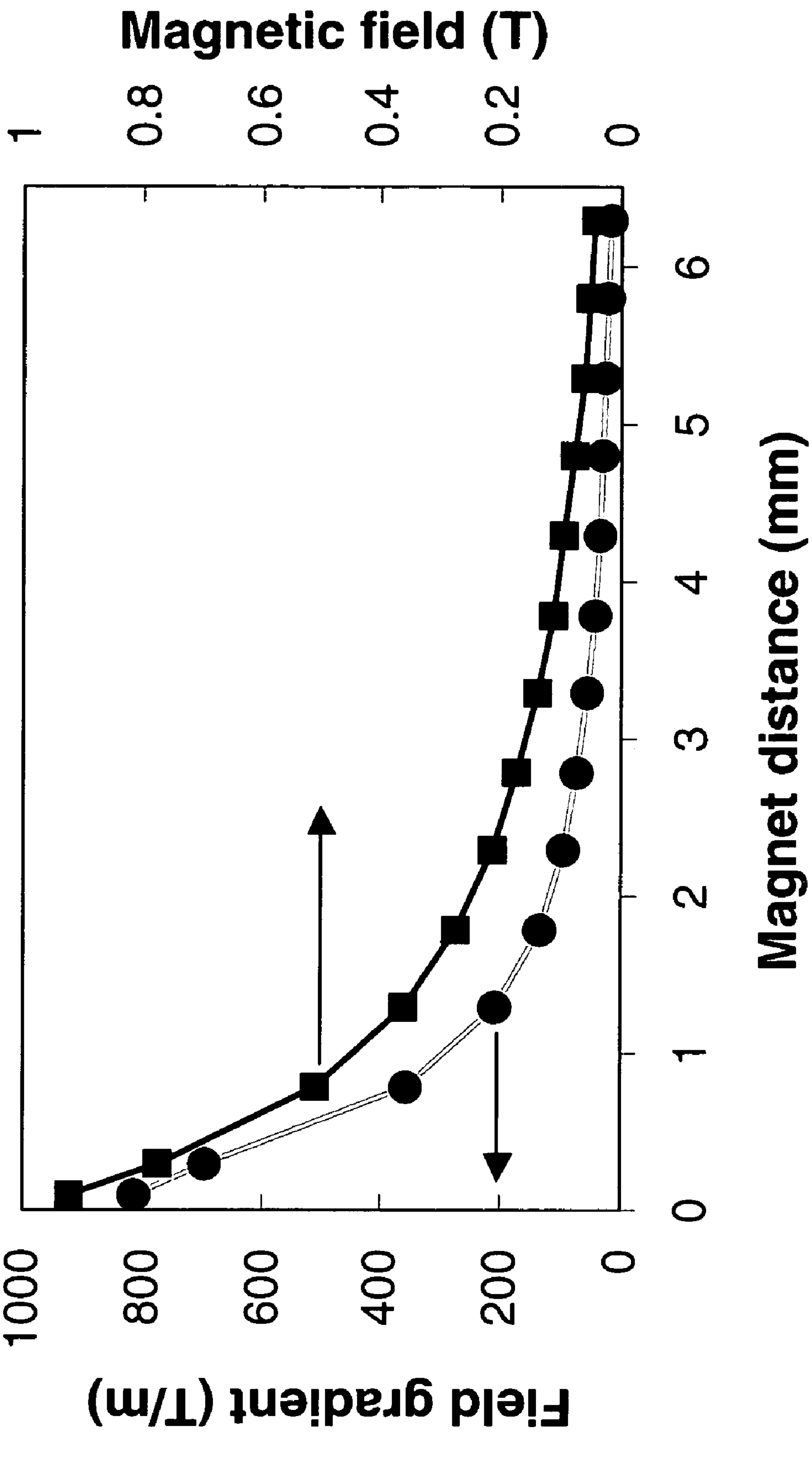
FIG. 9A is a graph showing the simulation results of magnetic field (blue square) and field gradient (red circle) when the gap between the poles is –0.8 mm. The arrows indicate which y scale to use for each graph.
Figure 9B:
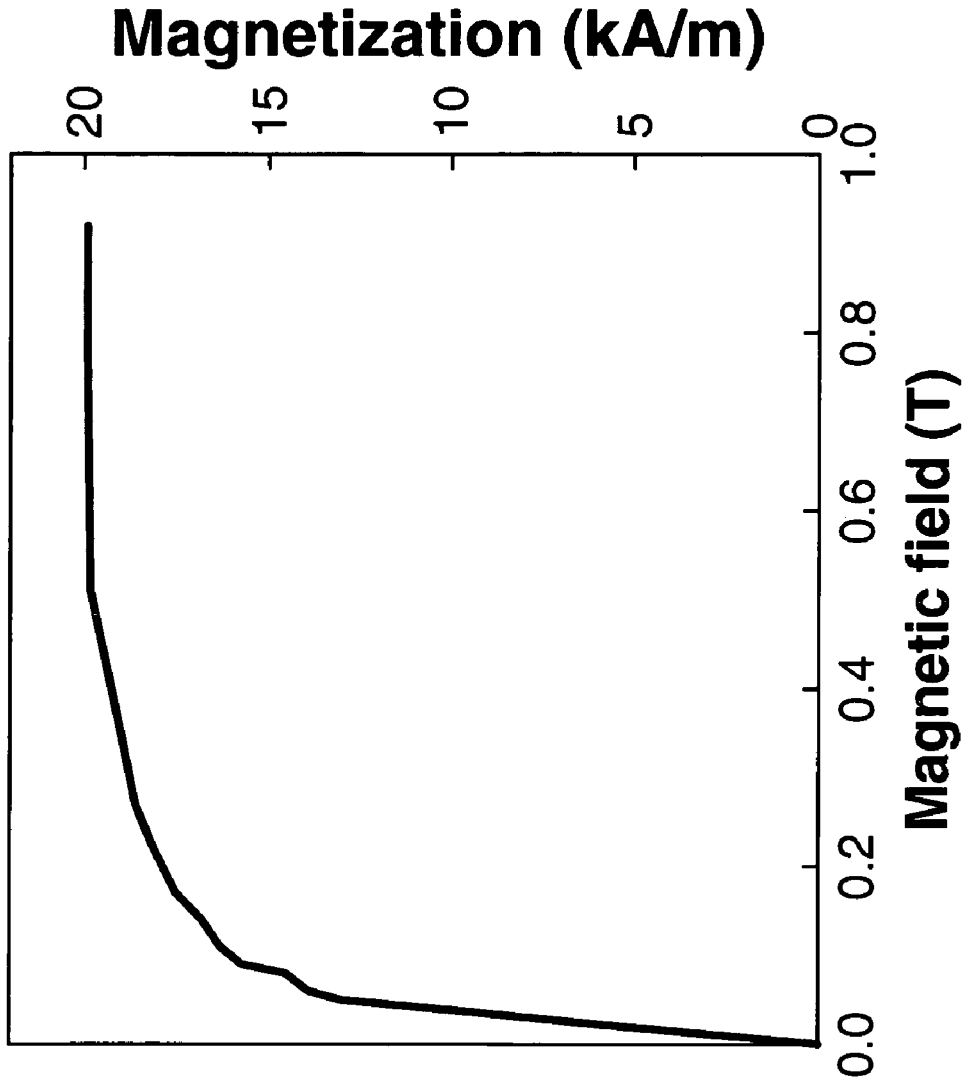
FIG. 9B is a graph showing the magnetization of a 4.5 μm magnetic bead vs. the external magnetic field.

FIGS. 8C and 8D shows the schematic diagram of the magnetic tweezers we constructed in greater detail. Some basic features were adopted from that previously reported (Strick, Allemand et al. 1996). DNA molecules inside the flow cell can be mechanically manipulated by applying force and torque with a pair of magnets to the magnetic bead attached to one end of the DNA. The magnets are attached to the bottom of a cylindrical spindle that has a hole in the middle for illumination of the flow cell. Rotation and translation of the magnet assembly are driven by two computer controlled (Polytec PI motor control card C-843) stepping motors with built-in position encoders (Polytec PI, M126.DG and C-136.10).

When operating the magnetic tweezers in bright field illumination mode, high intensity light from a fiber-coupled arc lamp (Thorlabs, OSL1) is filtered through a red bandpass filter (F-1) (Omega Optical), collimated by three lenses (L-1, L-2, and L3) and collected into a 100× oil-immersion objective (Zeiss Neofluar N.A.=1.3). Light from the objective is reflected off a 45° angle mirror (M–1; Thorlabs), passed through a dichroic mirror (M–2; Omega Optical), a focusing lens (L-4; Thorlabs), and imaged with either a Pixelfly (C-1; Cooke Corporation) or Watec (C-2) CCD camera. The image is easily switched between cameras with a flip-mirror (M-3) (Zeiss). Images from the Pixelfly and Watec CCD cameras are captured with the Pixelfly framegrabber (Cooke Corporation) or DT-3155 framegrabber (Data Translation Inc.), respectively. The Pixelfly camera is used to measure forces up to ~30 pN by Brownian fluctuations (Strick, Allemand et al. 1996) because it is non-interlaced and its data acquisition time can be very small (1 msec), which is advantageous in following fast fluctuations occurring in high force. To adjust the focus with nm precision, the objective lens was mounted on a closed-loop PIFOC objective positioner (Polytec PI) controlled by the E-662 controller chassis (Polytec PI) and a multifunction data acquisition card (Data Translation Inc., DT-322).

When operating the magnetic tweezers in epi-fluorescence mode, illumination from a Lambda LS arc lamp (Sutter LB-LS/OF17: 175 Watt) is passed through a neutral density filter (F-2) and an excitation filter (F-3; Omega Optical, XF1073), reflected off a dichroic mirror (M-2; Omega Optical, XF2010) and a 45° angle mirror (M–1; Thorlabs), and focused by the objective onto the experimental sample. Fluorescence is collected back into the objective, reflected off the 45° angle mirror (M–1), passed through the dichroic mirror (M–2), a focusing lens (L-4), and an emission filter (F-4; Omega Optical, XF3084), and imaged onto one of the CCD cameras as described above. The selection of these optical components is to detect green fluorescence induced by blue excitation.

To control flow levels during buffer exchange with high precision, we constructed a computer controlled micro-fluidics exchange system similar to one described elsewhere (Wuite, Davenport et al. 2000). Buffer from one of three bottles, selected with a high-pressure fluidics switch (S-1), can be delivered to the experiment. During data acquisition a second switch (S-2) closes off the fluidics system to prevent noise introduced by residual flow.

EXAMPLE 3

Characterization of the Field Gradients and Force of the Hybrid Magnetic Tweezers The hybrid magnetic tweezers were built according to Example 1 to extend the range of force with the device. FIG. 10A and Table 1 show a simulation result of magnetic field and field gradient along the z axis.

The simulation of the magnetic field at the tip agreed with the actual field measurement with a Hall probe to within 5%.

Table 1: Simulation results of magnetic field and field gradient vs. magnet distance. The zero magnet distance 0 is defined by the lowest position possible for the magnets. The force to a M500 bead was calculated based on the simulation.

| Distance (mm) | B (T) | Field gradient (T/m) | M (kA/m) | Force (pN) |
|---|---|---|---|---|
| 0.1 | 0.92 | 812.8 | 23.0 | 907.2 |
| 0.3 | 0.77 | 694.7 | 23.0 | 773.2 |
| 0.8 | 0.51 | 358.4 | 22.9 | 394.7 |
| 1.3 | 0.36 | 209.2 | 22.0 | 236.0 |

-continued

| Distance (mm) | B (T) | Field gradient (T/m) | M (kA/m) | Force (pN) |
|---|---|---|---|---|
| 1.8 | 0.27 | 133.5 | 21.5 | 153.0 |
| 2.3 | 0.22 | 97.3 | 20.9 | 106.4 |
| 2.8 | 0.17 | 73.2 | 20.2 | 84.6 |
| 3.3 | 0.14 | 57.1 | 19.4 | 61.7 |
| 3.8 | 0.11 | 44.9 | 18.8 | 46.0 |
| 4.3 | 0.09 | 36.8 | 18.1 | 42.5 |
| 4.8 | 0.08 | 30.6 | 16.8 | 32.3 |
| 5.3 | 0.06 | 25.3 | 16.1 | 24.7 |
| 5.8 | 0.05 | 21.0 | 15.0 | 18.6 |
| 6.3 | 0.04 | 17.8 | 12.1 | 21.0 |

The force to a magnetic bead is given as $$F_z = \frac{\partial}{\partial z}(MVB)$$

where M is the magnetization (M was calculated for M500 based on the magnetization data for M280 provided by Dynal Biotech.), V the volume of the bead (~$4.77\times10^{-17}$ $m^3$ for M500), and B the magnetic field. With the values in Table 1, the estimate of the force was calculated as shown in FIG. 12 and Table 1.

The vertical force to a magnetic bead is given as $$F_z = \frac{\partial}{\partial z}$$

(MVB) where M is the magnetization and V the volume of the bead (~$4.77\times10^{-17}$ $m^3$ for the 4.5 μm bead). M for a 4.5 μm bead vs. the external magnetic field B displayed in FIG. 10B was obtained by multiplying a similar curve for a 2.8 μm bead provided by Dynal Biotech by the ratio of maximum magnetizations of the two beads. The magnetization of the bead saturates at high external field because of its super-paramagnetic nature. Super-paramagnetic material appears paramagnetic at room temperature although it is ferromagnetic because its small domains are easily disordered by thermal energy due to large surface effects (Bodker, Morup et al. 1994). The magnetization of the super-paramagnetic material increases as the external field increases until it approaches the maximum magnetization that can be obtained in a well-aligned ferromagnetic crystal.

We performed a large number of cycles of such simulations and calculations by modifying the design of the magnets until we could not improve the estimate of the force. According to this estimate, the force exerted by the new magnet is ~900 pN with a 4.5 μm bead.

EXAMPLE 4

Force Measurement of Hybrid Magnetic Tweezers by DNA Over-Stretching Transitions In order to measure force experimentally and prove that indeed such high forces can be measured using the hybrid magnetic tweezers of Example 2, the following was performed. First, we took advantage of well-known overstretch transitions (OST) of double-stranded DNA molecules (Cluzel, Lebrun et al. 1996; Smith, Cui et al. 1996). A DNA molecule with nick experiences OST at the tension of 65 pN and a torsionally constrained DNA at 110 pN. We determined the magnet distances from the bead that yield 65 pN and 110 pN to two different magnetic beads, 2.8 μm (M280) and 4.5 Mm (M500) beads. Second, we measured force directly by grabbing magnetic beads (Dynal Biotech), attached to a flexible pipette, with the hybrid magnetic tweezers and measuring bendings of the pipette at various magnet distances. From the result obtained with OST of DNA, we calibrated the stiffness of the pipette because the force by the hybrid magnet tweezers is a function of the magnet distance. Once the stiffness of the pipette was known, the forces at different magnet positions were determined.

It is known that a double-stranded DNA molecule upon OST is elongated by 70% of its full extension (Cluzel, Lebrun et al. 1996; Smith, Cui et al. 1996; Leger 1999). This extension occurs upon application of an extension force of 65 pN to a DNA molecule with nick and at 110 pN to a torsionally constrained DNA. In order to make sure whether the DNA molecule under study is torsionally constrained or nicked, each DNA molecule was twisted by +75 and −75 turns, which corresponds to $$\sigma = \frac{Lk - Lk_0}{Lk_0} \sim$$

±5.3% where σ is supercoiling density and $Lk_0$ is the linking number of relaxed DNA and Lk the linking number of the molecule, and checked for supercoiling. If the DNA molecule is torsionally constrained, it will form plectonemic supercoils and appear to be shorter. If the molecule is nicked, twisting makes no difference.

For 4.5 μm magnetic beads, the overstretch transition of nucleic acids happens with the magnets ~2.8 mm away when DNA is nicked and ~2.1 mm away when DNA is torsionally constrained. For 2.8 μm beads, similar transition happens with the magnets 0.55 mm away for nicked DNA and ~0.2 mm away for torsionally constrained DNA.

According to the information provided by the manufacturer, the saturated magnetic dipole of a 4.5 μm bead is 5.5 times larger than that of a 2.8 μm bead based on the volume ratio ($4.5^3/2.8^3$) and the magnetic content ratio 1.33±0.3. In order to convert the forces on a 2.8 μm bead with the magnets 0.55 mm and 0.2 mm away to those exerted on a 4.5 μm bead, the transition forces (65 pN and 110 pN) were multiplied by the magnetic dipole ratio of the beads, 5.5. The converted force values (360±90 pN and 609±152 pN) are marked in FIG. 12.

EXAMPLE 5

Force Measurement by Elastic Bending of a Pippette

The bending of a pipette with a high force constant (typically ≧100 pN/μm) is a convenient way to measure high force (Leger 1999; Yan, Skoko et al. 2004).

For pipette bending experiments (see FIG. 8B), thin-walled hollow pipettes (World Precision Instruments: OD=1 mm) were pulled by a commercial pipette puller (Sutter P-97) and the flexibility of the taper was adjusted to be optimal by varying pulling conditions. The tip of the pipette (a few μm in diameter) was trimmed to be square by cutting the end with heated platinum wire, which affects the final stiffness of the pipette tip.

A tapered pipette as described above was inserted through glass tubing to the chamber in the flow cell where beads are available. Beads (4.5 μm beads) flowing by the pipette were captured by suction. By measuring bending of the pipette at the magnet positions (2 mm and 3 mm) around which a magnetic-bead-tagged DNA molecule undergoes OST, we determined that the stiffness of the pipette is 286±20 pN/μm. Since the pipette appears with diffraction fringes across the width (the inset (right) in FIG. 3A), the fringes were analyzed in much the same way as that for the round beads. We did not use the radial intensity profile by the captured bead because the fringe of the pipette tip interfered with its diffraction image.

With no magnetic force, a set of diffraction patterns of the pipette was generated for different distances between the pipette and the objective lens beneath the flow cell. Following the same procedure, the intensity profiles were converted to phase values ϕ and the relation between Z and ϕ. For various magnet positions, ϕ was measured and the vertical displacement of the pipette was calculated using the Z equation. The force on the captured bead was then the product of the stiffness and displacement of the pipette.

The inset in FIG. 12 shows the deflection of the pipette as a function of the magnet position. The stiffness of the pipette was determined by interpolating the pipette bending measurements at 2 mm and 3 mm to make comparison with the overstretch transitions of DNA attached to a 4.5 μm bead. The pipette obeys Hooke's law ($F_{mag}$=k·d, where k is the stiffness and d the deflection of the pipette under the magnetic force $F_{mag}$). For a narrow range of Z, the magnetic force can be empirically described as $F_{mag}=\alpha \cdot e^{-\beta Z}$. Therefore, $d(Z)=(\alpha/k) e^{-\beta Z}$ and $\beta=0.55\ mm^{-1}$ when d(2 mm)=0.38 μm and d(3 mm)=0.22 μm. Knowing that F at 2.1 mm ~110 pN and F at 2.8 mm ~65 pN from the DNA overstretch results, we determined that the best k value is 292±20 pN/μm. Once k is known, the deflection values can be converted to forces as shown in FIG. 12.

FIG. 12 displays the force values from the pipette measurements, DNA overstretch transitions, and simulation. The force estimations with 2.8 μm beads are in good agreement with the values obtained with the pipette method. Remarkably, the magnetic tweezers were able to apply ~900 pN with 4.5 μm beads and ~140 pN with 2.8 μm beads. This level of force has never been demonstrated before with magnetic tweezers and is ~7 times more force than obtained with magnetic tweezers with commonly available magnets. With such force enhancement, one can use 2-3 times smaller magnetic beads in practice to obtain the same level of force. Since the viscous frictional drag for a spherical object is related to its size by Stokes' formula, a 2-3 fold better time resolution is then obtained by choosing these smaller beads.

As shown in the figure, the force rapidly increases as the magnets approach the magnetic bead because the field gradient will increase in the proximity of the pole tips as shown in FIG. 10A. The force estimations with 2.8 μm beads show excellent agreements with the values obtained with the pipette method. The experimental results also show good agreement with the calculated force values (Table 1 and FIG. 12 (dotted line)) based on the simulations (FIG. 10A) with no adjustable parameter. It was rather unexpected because the field simulation and force calculation was based on a 2D model and the magnetization values converted from those for a 2.8 μm beads.

EXAMPLE 6

Hilbert Transformation Scheme

By using Hilbert transformation scheme, we can monitor enzymatic activity of proteins in real time with frequency of −20 Hz. The reason for high speed in this scheme is that it does not involve optimization that tends to be slower than algebraic calculation. The conformation of a DNA molecule in our magnetic tweezers is deduced from the position of the bead attached to it. We define a bead area as the bright area bounded by the first diffraction ring by the bead. Our framegrabber program (provided by Jan Liphardt and Nathan Clack) records all the contiguous pixels in the bead area starting from a seed pixel. By calculating the brightness-weighted center of a collection of such pixels, we can determine the center (X and Y) of the bead. This center serves as the seed for the next frame while the seed for the first frame is given by us. As long as the framegrabber program completes the task for each frame acquired, the bead remains tracked. If a seed is not in a bead area, this procedure fails and tracking is stopped.

Figure 11:
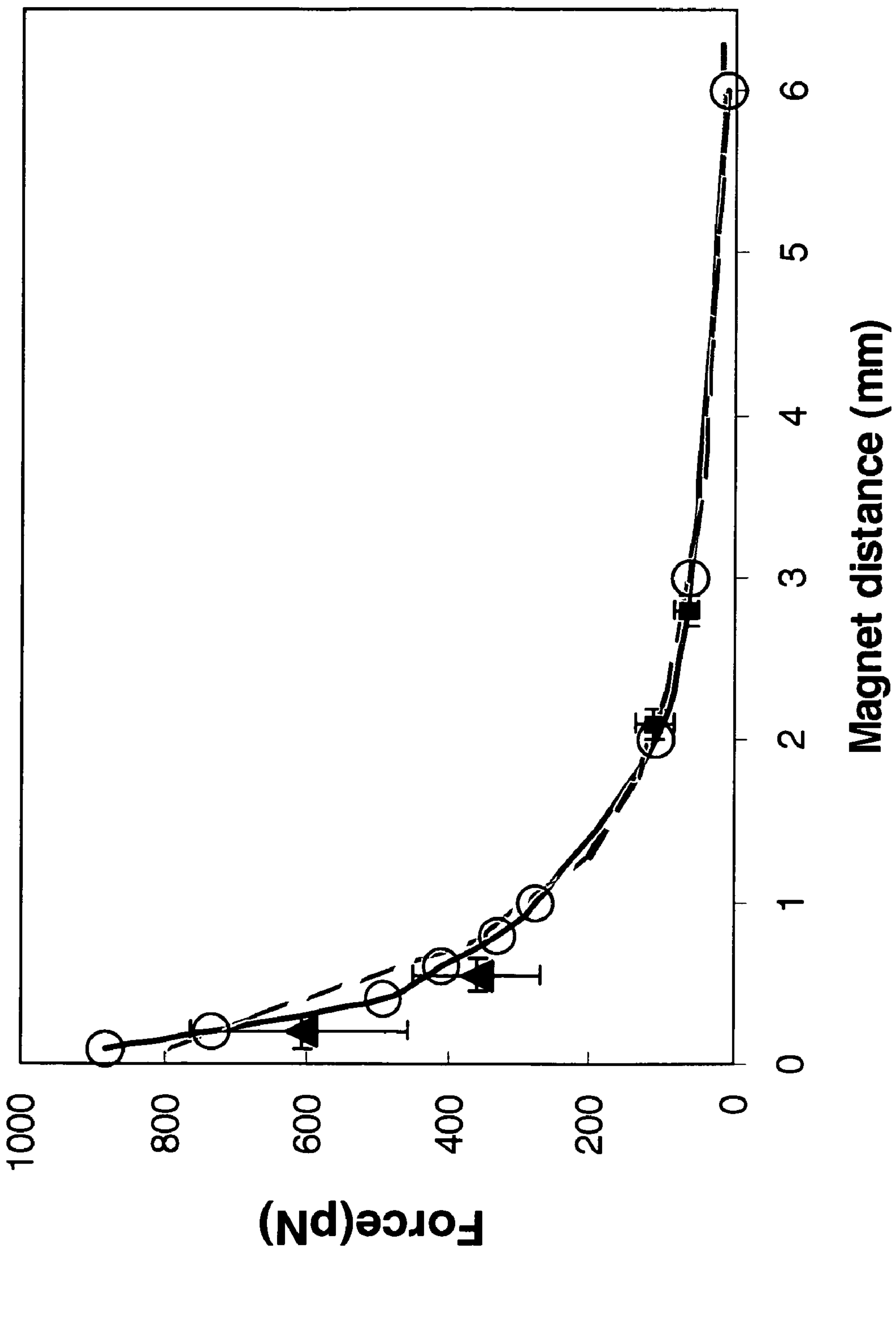
FIG. 11 shows a graph of magnet position vs. force. Red squares are the force values determined by OST with 4.5 μm bead. Blue circles guided by a line are the data obtained with pipette bending measurements. These data were calibrated against the OST data (with 4.5 μm bead). Green triangles are the force values measured by OST with 2.8 μm bead and scaled according to the magnetic dipole ratio. Dotted orange line is the force values based on the 2D simulation. The zero magnet distance is defined as the lowest position possible for the magnets.

The vertical position (Z) is determined by examining diffraction ring patterns cast by the bead onto the detector because the pattern varies as a function of the distance between the bead and the focal plane of the objective (See the inset in FIG. 11A (left)) (Gosse and Croquette 2002). To calibrate this behavior, we generated a set of diffraction ring patterns (FIG. 11A and inset) for known distances between the bead and the objective lens. The set was typically obtained by stepping the objective in 200 nm increments over a range of 5-10 microns.

To extract the radial intensity profile of the bead we first find the brightness-weighted center. Next, the distance from the bead center and the intensity value for each pixel are collected over one quadrant of the bead image with the center being the origin. These values are binned according to the distance from the bead center, using a bin size of a quarter of a pixel. We excluded the data in which the distance is closer than 8 times the pixel width because, with such small bin sizes, there may not be any data points in some bins near the center. Third, the intensity values assigned to each bin are then averaged to yield the radial intensity profile Q[x] where x is the bin index (FIG. 11A). For example, Q[0] is calculated from the pixels the distance of which is from 8 times the pixel width to 8¼ times the pixel width and Q[1] is from the next interval of the same width. Any remaining noise in the profile is removed by long-pass filtering with a discrete Fourier transform (DFT) (FIG. 11B). The filtered profile, Q[x], was shifted compared to Q[x] because the zero-frequency term after DFT was omitted in inverse DFT. Because the rings expand as the bead moves away from the focal plane of the objective, the phase of the oscillatory ring pattern will also vary accordingly.

We then apply to Q'[x] the Hilbert transformation that is often used in signal processing and nonlinear dynamics (Oppenheim 1989; Flesselles, Croquette et al. 1994) to rapidly get the necessary phase information from the oscillatory patterns. In our analysis, the size (N) of the data array in discrete Hilbert transformation (and discrete Fourier transformation) is 256 (=$2^8$) to utilize fast Fourier transformation. x therefore varies from 0 to 255. If P[k] is the DFT of $$Q'[x]\left(P[k]=\sum_{x=0}^{N-1} Q'[x]\cdot e^{(2\pi i/N)xk}\right)$$

and we choose the range of k to be from −127 to 128, its real part P[k] becomes an even sequence and its imaginary part $P_i[k]$ an odd sequence. In general, we can always construct a causal, stable sequence A[k] when we have either an even sequence or an odd sequence as follows. By assuming $$U[k]\equiv\left|\begin{array}{ll}1 & \text{when } k=0 \text{ and } N/2\\ 2 & \text{when } 0<k<N/2\\ 0 & \text{when } -N/2<k<0\end{array}\right.,$$

we get $$A[k]=P[k]-U[k]=(P_r[k]+iP_i[k])\cdot U[k]+P_{ro}'[k]+i(P_i[k]+P_{ie}'[k])$$

where the odd sequence $P_{ro}'[k]=P_r[k]\cdot U[k]-P_r[k]$ and the even sequence $$P_{ie}'[k]=P_i[k]-P_i[k].$$

Inverse DFT of A[k] is then $$\begin{aligned}H[x] &= \frac{1}{N}\sum_{k=-N/2+1}^{N/2} A[k]\cdot e^{-(2\pi i/N)xk} = \\ &\frac{1}{N}\sum_{k=-N/2+1}^{N/2}(P_r[k]+P_{ro}'[k]+iP_i[k]+iP_{ie}'[k])\cdot e^{-(2\pi i/N)xk} = \\ &\frac{1}{N}\sum_{k=-N/2+1}^{N/2} P[k]\cdot e^{-(2\pi i/N)xk} + \\ &\frac{i}{N}\sum_{k=-N/2+1}^{N/2}\left(P_{ie}'[k]\cos\left[\frac{2\pi ixk}{N}\right]-P_{ro}[k]\sin\left[\frac{2\pi ixk}{N}\right]\right)\equiv \\ &Q'[x]+iI[x].\end{aligned}$$

The phase $\Phi[x]=\tan^{-1}(I[x]/Q'[x])$ is the phase of H[x] (FIG. 3(*c*)). The inset in FIG. 11B illustrates the phase Φ[x] as the polar angle of the graph.

In order to increase the signal-to-noise ratio, we averaged Φ[x] over the range (from $x_1$ to $x_2$) over which the phase values change monotonously with $$Z\left(\varphi=\frac{1}{x_2-x_1+1}\sum_{x=x_1}^{x_2}\Phi[x]\right)$$

(see FIG. 11C).

The relation between ϕ and Z is determined by a polynomial fit, usually $3^{rd}$ order (due to the good linearity between ϕ and Z, a $1^{st}$ order fit is often sufficient): $Z=a\phi^3+b\phi^2+c\phi+d$ where a, b, c, and d are fitting parameters (see FIG. 11D). In experiments, the image captured by a framegrabber is quickly analyzed to yield the average phase ϕ). This phase ϕ is inserted into the Z equation so that Z can be displayed in real time. We tracked the bead and determined its vertical position in real time faster than 20 Hz.

The present structures, embodiments, examples, methods, and procedures are meant to exemplify and illustrate the invention and should in no way be seen as limiting the scope of the invention. Various modifications and variations of the described hybrid magnetic structure, methods of making, and applications and uses thereof of the invention will be apparent to those skilled in the art without departing from the scope and spirit of the invention.

Any patents or publications mentioned in this specification are indicative of levels of those skilled in the art to which the invention pertains and are hereby incorporated by reference to the same extent as if each was specifically and individually incorporated by reference

REFERENCES

Bodker, F., S. Morup, et al. (1994). "Surface effects in metallic iron nanoparticles." *Phys. Rev. Lett.* 72(2): 282-85.

Bryant, Z., M. D. Stone, et al. (2003). "Structural transitions and elasticity from torque measurements on DNA." *Nature* 424(6946): 338-41.

Bustamante, C., J. C. Macosko, et al. (2000). "Grabbing the cat by the tail: manipulating molecules one by one." *Nat Rev Mol Cell Biol* 1(2): 130-6.

Carrion-Vazquez, M., A. F. Oberhauser, et al. (1999). "Mechanical and chemical unfolding of a single protein: a comparison." *Proc Natl Acad Sci USA* 96(7): 3694-9.

Cluzel, P., A. Lebrun, et al. (1996). "DNA: an extensible molecule." *Science* 271(5250): 792-4.

Dekker, N. H., V. V. Rybenkov, et al. (2002). "The mechanism of type IA topoisomerases." *Proc Natl Acad Sci USA* 99(19): 12126-31.

Flesselles, J. M., V. V. Croquette, et al. (1994). "Period doubling of a torus in a chain of oscillators." *Physical Review Letters* 72(18): 2871-2874.

Forde, N. R., D. Izhaky, et al. (2002). "Using mechanical force to probe the mechanism of pausing and arrest during continuous elongation by *Escherichia coli* RNA polymerase." *Proc Natl Acad Sci USA* 99(18): 11682-7. Gosse, C. and V. Croquette (2002). "Magnetic tweezers: micromanipulation and force measurement at the molecular level." *Biophys J* 82(6): 3314-29.

Haber, C., Wirtz, D. (2000). "Magnetic tweezers for DNA manipulation." *Rev. Sci. Inst.* 71: 4561-4569.

Howard, J., A. J. Hudspeth, et al. (1989). "Movement of microtubules by single kinesin molecules." *Nature* 342 (6246): 154-8.

Humphries, D., Pollard, M., Elkin, C. (2001). New High Performance Hybrid Magnet Plates for Molecular Separation and Bio-Technology Applications. *LBNL*-56017.

Ishijima, A., T. Doi, et al. (1991). "Sub-piconewton force fluctuations of actomyosin in vitro." *Nature* 352(6333): 301-6.

Kishino, A. and T. Yanagida (1988). "Force measurements by micromanipulation of a single actin filament by glass needles." *Nature* 334(6177): 74-6.

LANL Poisson Superfish 7 is available at ftp://sfuser: ftpsuperfish@laacg1.lanl.gov/ with the username SFUSER and the password ftpsuperfish.

Leger, J. F., Romano, G., Sakar, A., Robert, J., Bourdieu, L., Chatenay, D., Marko, J. F. (1999). "Structural transitions of a twisted and stretched DNA molecule." *Phys. Rev. Lett.* 83: 1066-1069.

Leuba, S. H., M. A. Karymov, et al. (2003). "Assembly of single chromatin fibers depends on the tension in the DNA molecule: magnetic tweezers study." *Proc Natl Acad Sci USA* 100(2): 495-500.

Liphardt, J., B. Onoa, et al. (2001). "Reversible unfolding of single RNA molecules by mechanical force." *Science* 292 (5517): 733-7.

Ludwig, M. (1999). "AFM, a tool for single-molecule experiments." *Appl. Phys. Mater. Sci. Process.* 68: 173-176.

Marko, J. F., Siggia, E. D. (1995). "Stretching DNA." *Macromolecules* 28: 8759-8770.

Mehta, A. D., M. Rief, et al. (1999). "Biomechanics, one molecule at a time." *J Biol Chem* 274(21): 14517-20.

Nakajima, H., Y. Kunioka, et al. (1997). "Scanning force microscopy of the interaction events between a single molecule of heavy meromyosin and actin." *Biochem Biophys Res Commun* 234(1): 178-82.

Oppenheim, A. V., Schafer, R. W., Buck, J. R. (1989). Discrete-time signal processing. Englewood Cliffs, N.J., Prentice Hall.

Perkins, T. T., D. E. Smith, et al. (1995). "Stretching of a single tethered polymer in a uniform flow." *Science* 268 (5207): 83-7.

Rief, M., M. Gautel, et al. (1997). "Reversible unfolding of individual titin immunoglobulin domains by AFM." *Science* 276(5315): 1109-12.

Rouzina, I. and V. A. Bloomfield (2001). "Force-induced melting of the DNA double helix 1. Thermodynamic analysis." *Biophys J* 80(2): 882-93.

Rouzina, I. and V. A. Bloomfield (2001). "Force-induced melting of the DNA double helix. 2. Effect of solution conditions." *Biophys J* 80(2): 894-900.

Smith, D. E., S. J. Tans, et al. (2001). "The bacteriophage straight phi29 portal motor can package DNA against a large internal force." *Nature* 413(6857): 748-52.

Smith, S. B., Y. Cui, et al. (1996). "Overstretching B-DNA: the elastic response of individual double-stranded and single-stranded DNA molecules." *Science* 271(5250): 795-9.

Smith, S. B., L. Finzi, et al. (1992). "Direct mechanical measurements of the elasticity of single DNA molecules by using magnetic beads." *Science* 258(5085): 1122-6.

Stone, M. D., Z. Bryant, et al. (2003). "Chirality sensing by *Escherichia coli* topoisomerase IV and the mechanism of type II topoisomerases." *Proc Natl Acad Sci USA* 100(15): 8654-9.

Strick, T. R., J. F. Allemand, et al. (1996). "The elasticity of a single supercoiled DNA molecule." *Science* 271(5257): 1835-7.

Strick, T. R., J. F. Allemand, et al. (1998). "Behavior of supercoiled DNA." *Biophys J* 74(4): 2016-28.

Strick, T. R., V. Croquette, et al. (2000). "Single-molecule analysis of DNA uncoiling by a type II topoisomerase." *Nature* 404(6780): 901-4.

Svoboda, K. and S. M. Block (1994). "Biological applications of optical forces." *Annu Rev Biophys Biomol Struct* 23: 247-85.

Svoboda, K., C. F. Schmidt, et al. (1993). "Direct observation of kinesin stepping by optical trapping interferometry." *Nature* 365(6448): 721-7.

Wuite, G. J., R. J. Davenport, et al. (2000). "An integrated laser trap/flow control video microscope for the study of single biomolecules." *Biophys J* 79(2): 1155-67.

Wuite, G. J., S. B. Smith, et al. (2000). "Single-molecule studies of the effect of template tension on T7 DNA polymerase activity." *Nature* 404(6773): 103-6.

Yan, J., D. Skoko, et al. (2004). "Near-field-magnetic-tweezer manipulation of single DNA molecules." *Phys Rev E* 70: 011905.

Zhuang, X., L. E. Bartley, et al. (2000). "A single-molecule study of RNA catalysis and folding." *Science* 288(5473): 2048-51.

Zlatanova, J. and S. H. Leuba (2003). "Magnetic tweezers: a sensitive tool to study DNA and chromatin at the single-molecule level." *Biochem Cell Biol* 81(3): 151-9.

What is claimed:

1. Hybrid magnetic tweezers comprising paired mirror image hybrid magnetic structures, wherein each of said hybrid magnetic structures comprising:

a. a non-magnetic base;

b. a ferromagnetic pole having a wedge-shaped tip, wherein said tip features a notch or concavity in cross-section to concentrate magnetic fields in a discrete region of interest inside the notch or concavity;

c. at least two blocks of permanent magnet material;

wherein the at least two blocks of permanent magnet material are assembled onto said base on opposite sides of and adjacent to said ferromagnetic pole, wherein the magnetization orientations of the blocks of permanent magnet material are oriented in opposing directions and orthogonal to the height of the ferromagnetic pole, and said blocks of permanent magnet material extend below the bottom edge of said ferromagnetic pole when assembled onto said base; and, wherein the ferromagnetic pole tip extends beyond each block of permanent magnet material, wherein the shaped tip is angled or bent from 0 to 90 degrees relative to the ferromagnetic pole, and wherein the magnetic field strength in the region of interest at least 1.0 Tesla.

2. The hybrid magnetic tweezers of claim 1, further comprising a clevis, wherein the clevis is a multi-walled housing and the hybrid magnetic tweezers are mounted therein, and wherein the hybrid magnetic tweezers can be moved to different Z positions or angles by rotation, translation and movement in the clevis using various means for fastening the hybrid magnetic tweezers to the clevis and/or means for orientation and position control, thereby resulting in various ranges of force in three-dimensions to be applied to a target.

3. The hybrid magnetic structure of claim 1, further comprising a flow vessel having a target.

4. The hybrid magnetic structure of claim 3, wherein the target is a magnetized molecule or particle.

5. The hybrid magnetic structure of claim 1, wherein said pole tip has a wedge shape in cross section and a notch of about 0.5 mm in depth in cross section at the tip.

6. The hybrid magnetic structure of claim 1, wherein said pole tip is angled about 45 degrees relative to the ferromagnetic pole.

7. The hybrid magnetic structure of claim 1, wherein the non-magnetic base is aluminum.

8. The hybrid magnetic structure of claim 1, wherein the ferromagnetic pole is made of steel.

9. The hybrid magnetic structure of claim 1, wherein the blocks of permanent magnet material comprise a rare earth element.

10. The hybrid magnetic structure of claim 9, wherein the blocks of permanent magnet material comprise neodymium iron boron.

11. A method of manipulating magnetized molecular particles from a sample, comprising the steps of:

placing said sample containing magnetized molecular particles in the region of interest of the hybrid magnetic tweezer of claim 1.

12. The method of claim 11, wherein the samples contain DNA coupled to a ferromagnetic material.

* * * * *